United States Patent
Norton et al.

(10) Patent No.: US 10,695,496 B2
(45) Date of Patent: Jun. 30, 2020

(54) METHOD OF FILLING CUSTOM SYRINGE

(71) Applicant: West Pharma. Services IL, Ltd., Ra'anana (IL)

(72) Inventors: Paul H. Norton, St. Augustine, FL (US); Oz Cabiri, Hod Hasharon (IL); Ran Hezkiahu, Herzliya (IL); Hubert Jansen, Stolberg (DE)

(73) Assignee: WEST PHARMA. SERVICES IL, LTD., Ra'anana (IL)

( * ) Notice: Subject to any disclaimer, the term of this patent is extended or adjusted under 35 U.S.C. 154(b) by 71 days.

(21) Appl. No.: 15/766,519

(22) PCT Filed: Oct. 10, 2016

(86) PCT No.: PCT/US2016/056210
§ 371 (c)(1),
(2) Date: Apr. 6, 2018

(87) PCT Pub. No.: WO2017/062930
PCT Pub. Date: Apr. 13, 2017

(65) Prior Publication Data
US 2018/0296762 A1   Oct. 18, 2018

Related U.S. Application Data

(63) Continuation of application No. 15/269,248, filed on Sep. 19, 2016, now Pat. No. 10,086,145, and a
(Continued)

(51) Int. Cl.
*B65D 25/10* (2006.01)
*A61M 5/28* (2006.01)
(Continued)

(52) U.S. Cl.
CPC ............ *A61M 5/28* (2013.01); *A61M 5/3134* (2013.01); *A61M 5/3202* (2013.01);
(Continued)

(58) Field of Classification Search
CPC ...... A61M 5/008; A61M 5/28; A61M 5/3204; A61M 5/34; A61M 5/3134; A61M 5/3202;
(Continued)

(56) References Cited

U.S. PATENT DOCUMENTS 1,125,887 A   1/1915   Schimmel
1,321,550 A   11/1919  Platt
(Continued)

FOREIGN PATENT DOCUMENTS

DE   855313 C    11/1952
EP   2364739 A1   9/2011
(Continued)

OTHER PUBLICATIONS

Int'l Search Report and Written Opinion dated Dec. 2, 2016 in Int'l Application No. PCT/US2016/056210.
(Continued)

*Primary Examiner* — Matthew W Jellett
(74) *Attorney, Agent, or Firm* — Panitch Schwarze Belisario & Nadel LLP

(57) ABSTRACT

A cartridge comprising a reservoir part and an extension extending from said reservoir part, said extension defining a fluid path and comprising a molding and a first needle extending from said molding, the extension turning to a finite angle with respect to an axis of said reservoir part and wherein at least part of said first needle is likewise at said finite angle, at least some of said part of said first needle at said finite angle being enclosed within said molding of said fluid path. A drug delivery device may be used with the cartridge and includes a skin-contacting surface. In use the longitudinal axis of the interior of the cartridge may be disposed substantially parallel to the skin-contacting surface.

27 Claims, 23 Drawing Sheets

Related U.S. Application Data continuation of application No. 15/204,542, filed on Jul. 7, 2016, said application No. 15/269,248 is a continuation-in-part of application No. 14/861,478, filed on Sep. 22, 2015, now Pat. No. 9,987,432.

(60) Provisional application No. 62/281,536, filed on Jan. 21, 2016, provisional application No. 62/284,806, filed on Oct. 9, 2015.

(51) Int. Cl.

| | | |
|---|---|---|
| *A61M 5/32* | (2006.01) | |
| *A61M 5/31* | (2006.01) | |
| *A61M 5/34* | (2006.01) | |
| *B65D 1/36* | (2006.01) | |
| *B65D 5/50* | (2006.01) | |
| *B65D 21/02* | (2006.01) | |
| *A61M 5/142* | (2006.01) | |
| *A61M 5/158* | (2006.01) | |
| *A61M 5/145* | (2006.01) | |

(52) U.S. Cl.
CPC ............ *A61M 5/3204* (2013.01); *A61M 5/34* (2013.01); *B65D 1/36* (2013.01); *B65D 5/503* (2013.01); *B65D 21/0233* (2013.01); *B65D 25/108* (2013.01); *A61M 5/1456* (2013.01); *A61M 5/14248* (2013.01); *A61M 2005/1581* (2013.01); *A61M 2005/312* (2013.01); *A61M 2005/341* (2013.01); *A61M 2205/3306* (2013.01); *A61M 2207/00* (2013.01)

(58) Field of Classification Search
CPC ............ A61M 5/1456; A61M 5/14248; A61M 5/344; A61M 5/3129; A61M 5/001; A61M 2205/3306; A61M 2205/1581; A61M 2205/341; A61M 2205/312; A61M 2207/00; B65D 1/36; B65D 5/503; B65D 21/0233; B65D 25/108; B65B 3/003
USPC .......................... 206/366, 486, 488, 490, 514
See application file for complete search history.

(56) References Cited

U.S. PATENT DOCUMENTS

| | | |
|---|---|---|
| 4,710,178 A | 12/1987 | Henri et al. |
| 5,275,582 A | 1/1994 | Wimmer |
| 5,456,360 A * | 10/1995 | Griffin ............... B01L 9/06 206/443 |
| 5,858,001 A | 1/1999 | Tsals et al. |
| 6,186,979 B1 | 2/2001 | Dysarz |
| 6,189,292 B1 | 2/2001 | Odell et al. |
| 6,500,150 B1 | 12/2002 | Gross et al. |
| 6,719,141 B2 | 4/2004 | Heinz et al. |
| 6,824,529 B2 | 11/2004 | Gross et al. |
| 6,843,782 B2 | 1/2005 | Gross et al. |
| 6,907,679 B2 * | 6/2005 | Yarborough ........ A61M 5/002 34/285 |
| 7,967,795 B1 | 6/2011 | Cabiri |
| 8,490,790 B2 * | 7/2013 | Cocheteux ........ A61M 5/008 206/364 |
| 8,496,862 B2 | 7/2013 | Zelkovich et al. |
| 8,603,028 B2 | 12/2013 | Mudd et al. |
| 8,721,603 B2 | 5/2014 | Lundquist |
| 9,539,757 B2 * | 1/2017 | Ramirez ............ B65B 5/068 |
| 9,862,519 B2 * | 1/2018 | Deutschle ......... B65D 25/108 |
| D838,367 S * | 1/2019 | Norton ............... D24/130 |
| 10,227,161 B2 * | 3/2019 | Auerbach ......... A61M 5/008 |
| 2005/0154353 A1 | 7/2005 | Alheidt |
| 2009/0093792 A1 | 4/2009 | Gross et al. |
| 2012/0118777 A1 * | 5/2012 | Kakiuchi ........... A61M 5/002 206/366 |
| 2013/0131589 A1 | 5/2013 | Mudd et al. |
| 2013/0253434 A1 | 9/2013 | Cabiri |
| 2014/0163526 A1 | 6/2014 | Cabiri et al. |
| 2015/0112278 A1 | 4/2015 | Ray et al. |
| 2015/0157806 A1 | 6/2015 | Knutsson |
| 2019/0071217 A1 * | 3/2019 | Brown ............... A47J 47/08 |

FOREIGN PATENT DOCUMENTS

| | | |
|---|---|---|
| EP | 2452708 A1 | 5/2012 |
| WO | 9721457 A1 | 6/1997 |
| WO | 2005070485 A1 | 8/2005 |
| WO | 2009043000 A1 | 4/2009 |
| WO | 2011110872 A1 | 9/2011 |
| WO | 2013036602 A1 | 3/2013 |
| WO | 2016087626 A1 | 6/2016 |
| WO | 2016087627 A1 | 6/2016 |

OTHER PUBLICATIONS

Written Opinion dated Sep. 25, 2017 in Int'l Application No. PCT/US2016/056210.
Int'l Preliminary Report on Patentability dated Jan. 18, 2018 in Int'l Application No. PCT/US2016/056210.

* cited by examiner

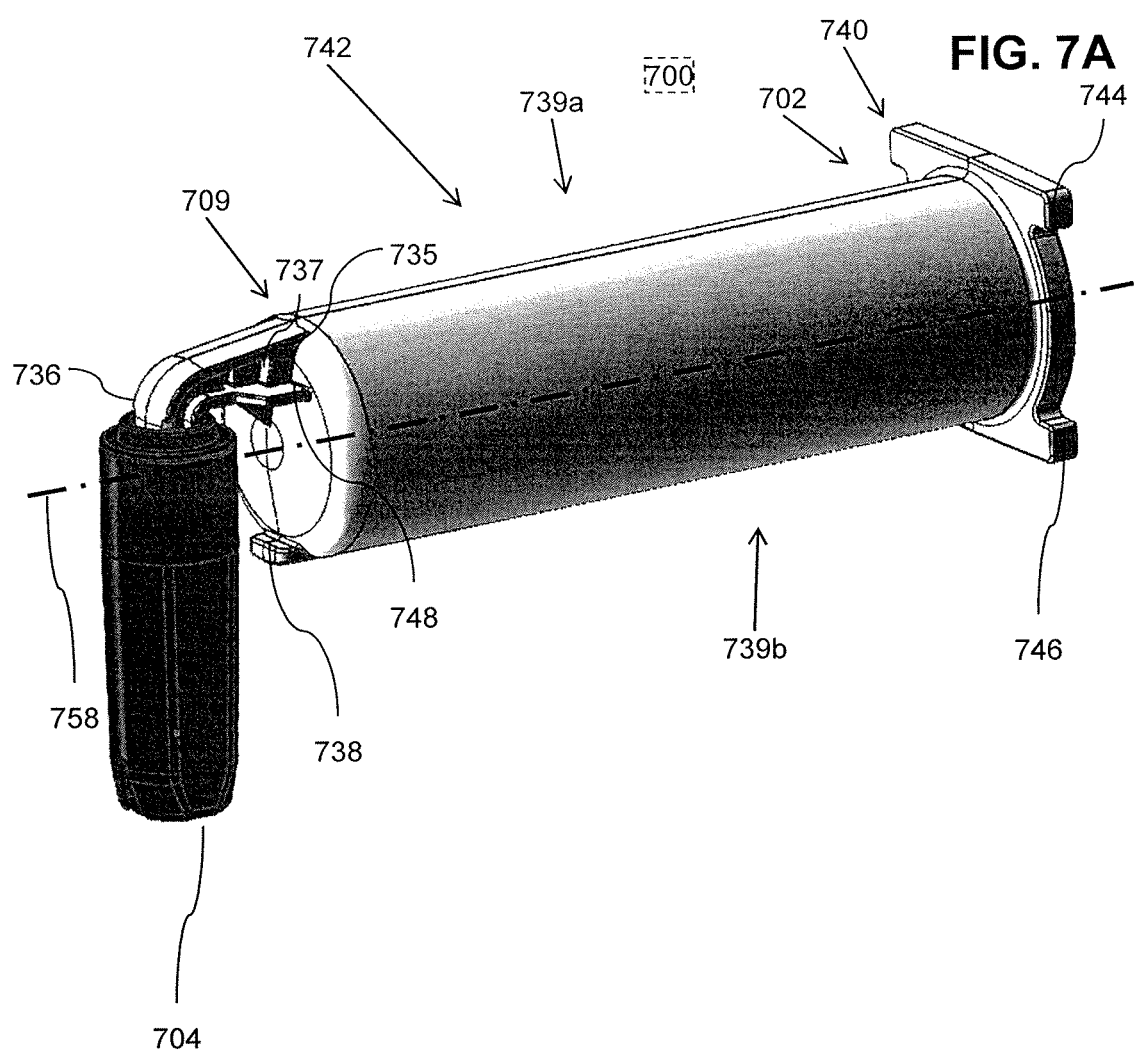

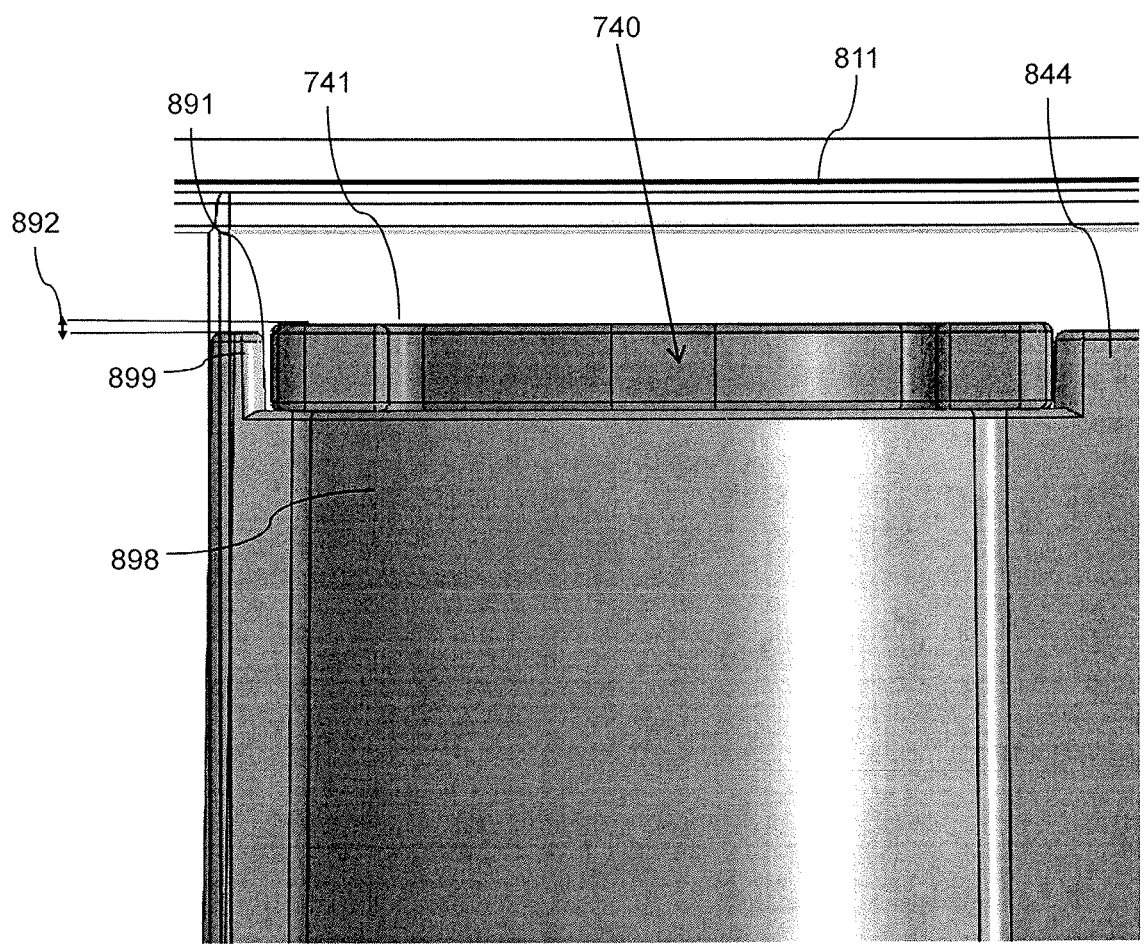

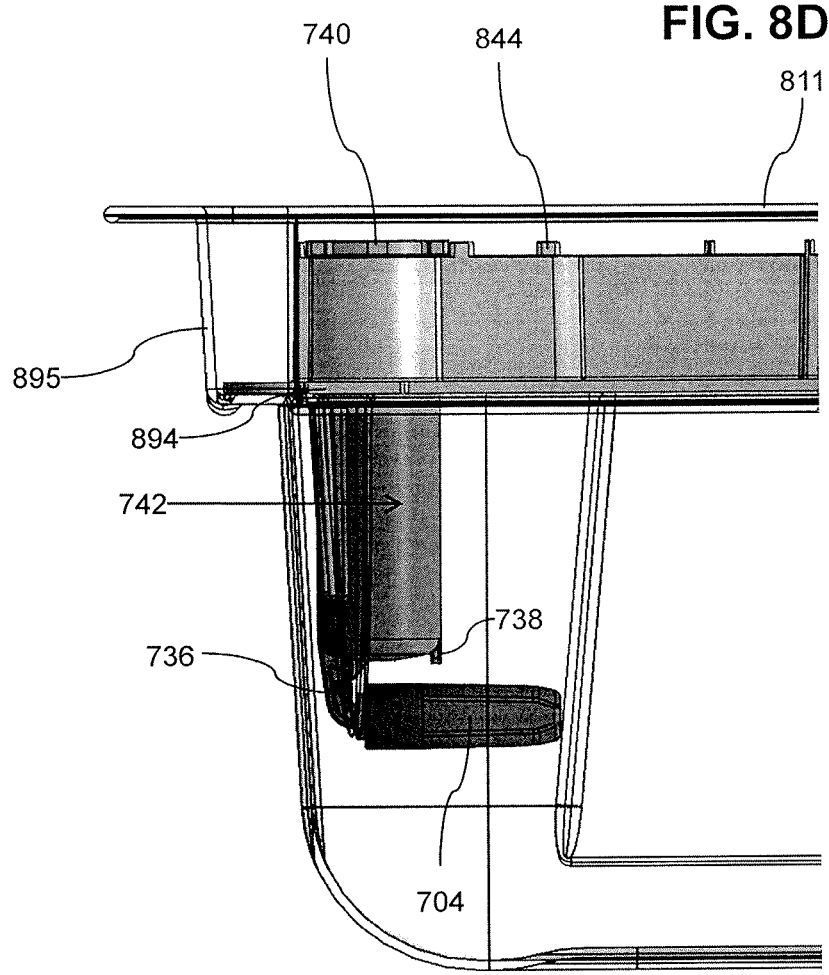

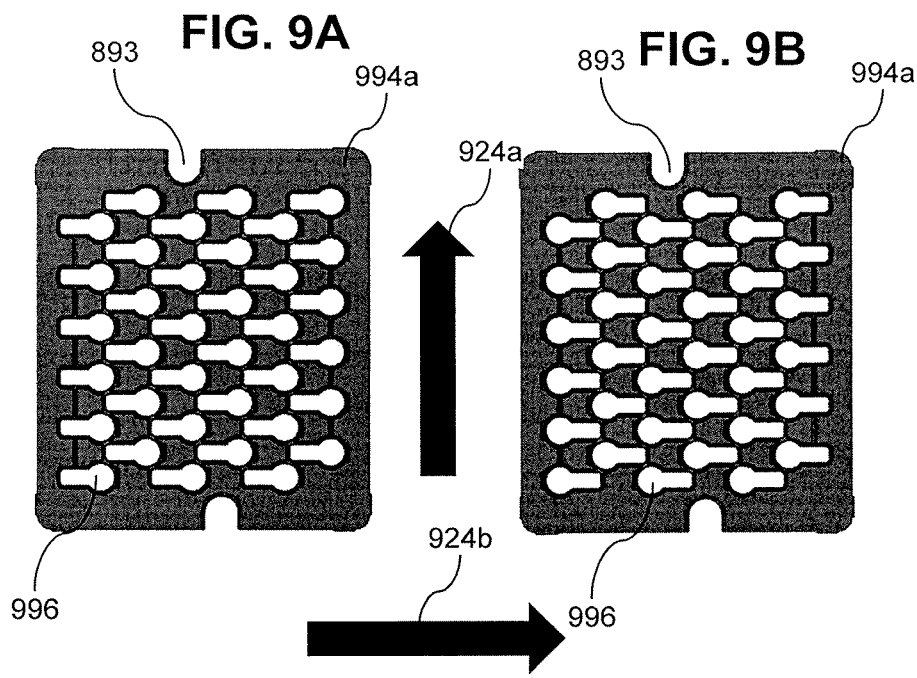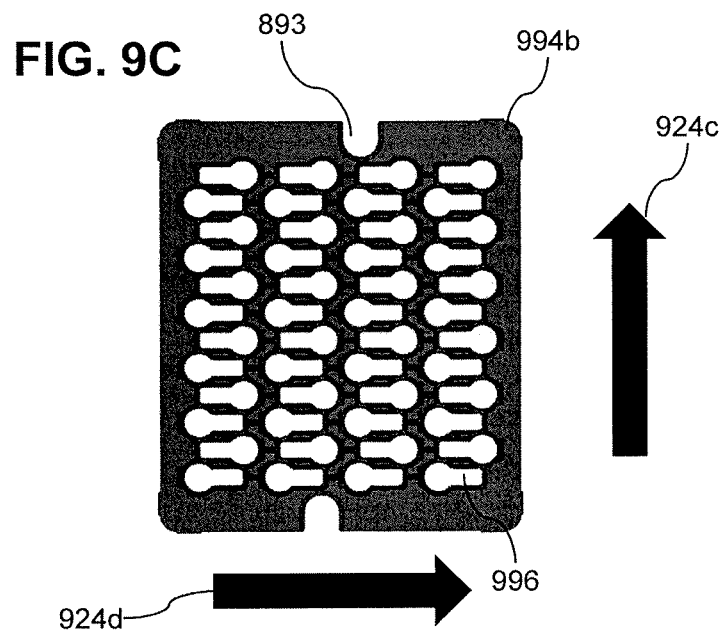

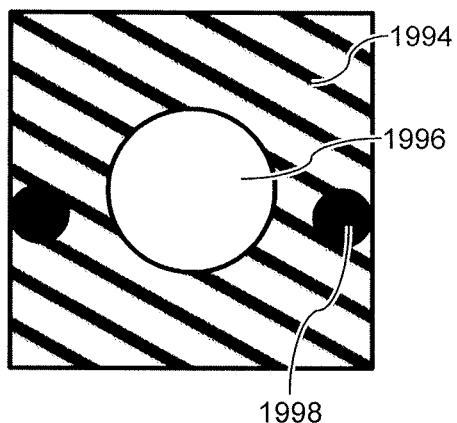
FIG. 19A
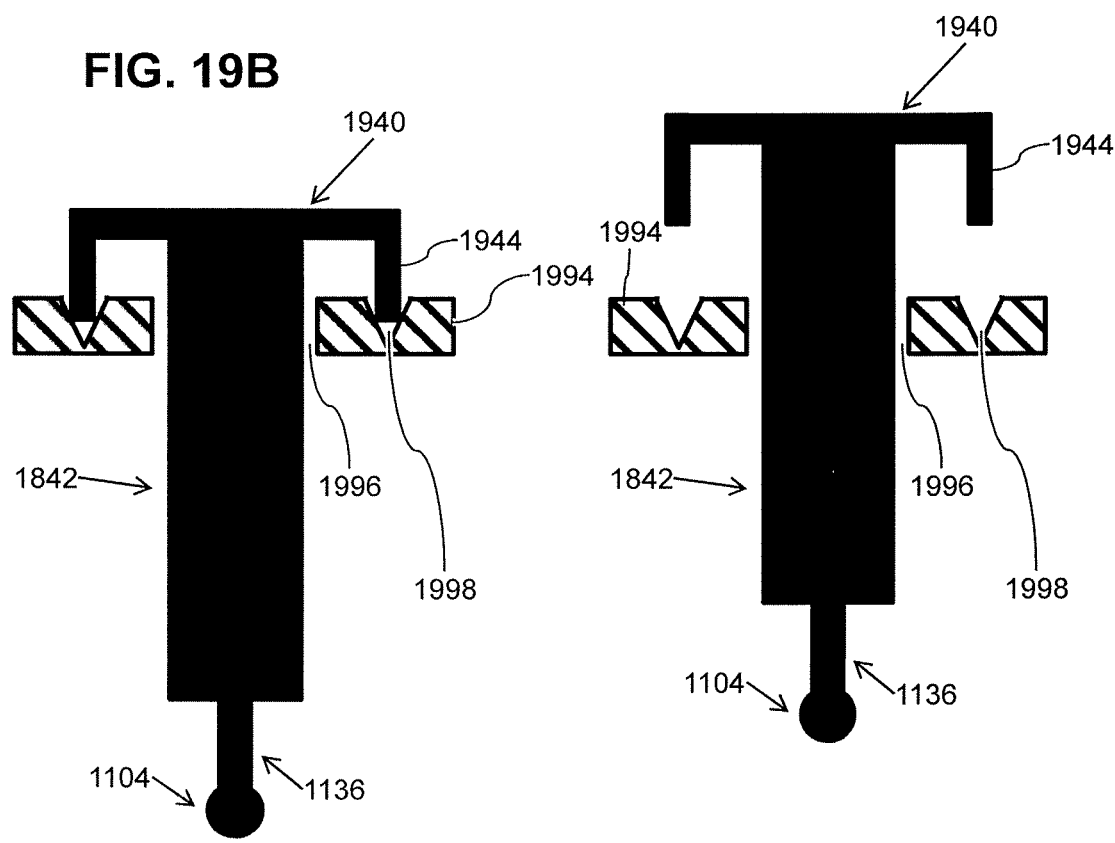
FIG. 19B
FIG. 19C

METHOD OF FILLING CUSTOM SYRINGE

This application is a section 371 of International Application No. PCT/US16/56210, filed Oct. 10, 2016, which was published Apr. 13, 2017 under International Publication No. WO 2017/062930 A 1, which is a continuation of U.S. application Ser. No. 15/204,542, filed Jul. 7, 2016, which claims the benefit of U.S. Provisional Application No. 62/281,536, filed Jan. 21, 2016 and U.S. Provisional Application No. 62/284,806, filed Oct. 9, 2015; and a continuation of U.S. application Ser. No. 15/269,248, filed on Sep. 19, 2016, the disclosures of which are incorporated herein by reference.

FIELD AND BACKGROUND OF THE INVENTION

The present invention, in some embodiments thereof, relates to filling of a non-standard syringe and, more particularly, but not exclusively, to automated filling a sterile medicine cartridge with a lateral projection.

U.S. Pat. No. 6,719,141 appears to disclose, "The device for transporting, filling and sterilizing medicinal containers (3) includes a rigid foamed plastic syringe nest (1) provided with a plurality of first openings (2) for receiving the respective containers (3). The first openings have respective open cross-sections adapted to corresponding cross-sections of the containers and the rigid syringe nest (1) has a predetermined thickness, so that the containers (3) are clamped and held fixed in position relative to the syringe nest and centered in the first openings (2) without rattling so that no scratch marks and/or no static charges are produced on the medicinal containers (3) during transport. The rigid foamed plastic syringe nest (1) is provided with a pore-free sealed surface that facilitates sterilization. Second openings (20), which are smaller than the first opening (2) and cannot receive the containers, are also provided in the syringe nest to facilitate sterilization in an autoclave."

International Patent Application Publication no. 2016087627 appears to disclose, "A device (1) for closing a chamber of a container having an opening for accessing the chamber comprises a plunger, a plunger seat (11), a container carrier (13) and a spacer (12). The plunger seat (11) releasably holds the plunger in a predefined alignment. The container carrier (13) is arranged to be connected to the container in a predefined position and alignment in relation to the opening of the container. The spacer (12) is arranged to position and align the plunger seat (11) adjacent to and distant from the container carrier (13) such that the opening of the container is open when the container is connected to the container carrier (13)."

U.S. Pat. Nos. 6,500,150, 6,824,529, and 6,843,782, appear to disclose a drug delivery device having a base member defining a skin-contacting surface, a syringe serving as a reservoir for the drug, and means for expelling drug from the syringe. The syringe is connected to the base member such that the longitudinal axis of the syringe is substantially parallel to the skin surface. A delivery needle is in communication with the syringe. The needle has an angled bend, which directs the tip of the needle substantially perpendicular to the skin-contacting surface. In use, the tip of the needle is adapted to penetrate the skin of the subject.

U.S. Pat. No. 5,858,001 appears to disclose a liquid drug delivery device adhered to the skin of a subject by a base member defining a skin-contacting surface having an adhesive coating. A columnar cartridge serves as reservoir for the drug and is incorporated in a housing, which is connected to the base member such that in use the longitudinal axis of the cartridge is disposed substantially parallel to the skin-contacting surface. A delivery needle communicating in use with the interior of the cartridge penetrates the skin of the subject when the housing snaps downward relative to the base member. This action also causes the actuation of a citric acid/sodium bicarbonate gas generator, which generates a gas to move a piston within the cartridge, compressing the drug compartment. This compression causes a stopper to be penetrated by a conduit in communication with the delivery needle, allowing the drug to be ejected from the compartment through the needle and into the subcutaneous tissue of the subject.

U.S. Patent Publication No. 20140163526 appears to disclose an automated injection device, which may be loaded with a standard type syringe and/or hypodermic needle. Optionally the syringe may be preloaded. The syringe may be loaded into the injector in a sterile state with needle cover in place. The injector includes a fastener, such as an adhesive base. The fastener may assist a user to hold the injector steady on the skin of a patient for an extended period. For example, the injector may be used to give injections of volume ranging between 0.5 and 3.0 ml over a time period ranging between 30 seconds and 10 minutes.

U.S. Pat. No. 1,125,887 relates to providing "a syringe needle with a bendable guard or shield that permits of a needle being safely bent to a desired angle or inclination, without danger of the needle being injured, cracked, or the walls thereof collapsed by the pliers or instrument employed for bending the needle."

U.S. Pat. No. 8,603,028 relates to a "handheld injection device includes a first housing having a first axis and a second housing having a second axis. In one embodiment, the second housing is configured to support a needle. In one embodiment, the first axis and a second axis form an adjustable angle between about 180 degrees and about 90 degrees."

U.S. Pat. No. 8,721,603 relates that, "A prefilled syringe for injecting medicament into a patient includes a barrel constructed of a polymeric material, a cannula and a hub. The barrel has a diameter, a longitudinal axis, a proximal end and a distal end. The cannula has a proximal end and a tip opposite the proximal end. The proximal end of the cannula is fixed to the distal end of the barrel. The cannula is positioned generally coaxially with the longitudinal axis. The hub is integrally formed with the distal end. The hub includes a rib section and a cap. The rib section has a generally cruciform cross-section taken along a rib plane. The rib plane is generally perpendicular to the longitudinal axis. The cap has a generally U-shaped cross-section taken along a longitudinal plane. The longitudinal plane is generally parallel to the longitudinal axis."

Additional background art includes U.S. Pat. No. 6,189,292. U.S. Patent. Publication No. 20130253434, U.S. Patent Publication No. 2009/093,792, U.S. Pat. No. 7,967,795, International Patent Application Publication no. 2016087626.

SUMMARY OF THE INVENTION

According to an aspect of some embodiments of the invention, there is provided a syringe comprising: a body including a reservoir having a longitudinal axis; an extension extending from a distal end of the body, the extension including: an annular sealing ring for a sterile sealing cap the sealing ring having an axis oriented at an angle ranging between 30 to 150 degrees with respect the longitudinal axis of the reservoir, and a fluid path passing through at least a portion of the extension, at least a portion of the path circumscribed by the sealing ring.

According to an aspect of some embodiments of the invention, there is provided a method for filling an elongated cartridge having an opening in a proximal end thereof to an end of a cylindrical bore; the cartridge having a proximal portion; the cartridge including a lateral protrusion located distal to the proximal portion; the method comprising: providing a syringe nest with a plurality of apertures therethrough arranged in a horizontal array; Inserting the lateral protrusion and a distal portion of the cartridge through an aperture of the plurality of apertures while an axis of the cylindrical bore remains vertical; Hanging the cartridge from the syringe nest with the axis vertical and the distal portion of the cartridge and the lateral protrusion extending below the aperture and extending laterally past an edge of the cylindrical bore.

According to some embodiments of the invention, the proximal portion of the cartridge includes a flange and each aperture is larger than an outer dimension the cartridge immediately distal to the flange.

According to some embodiments of the invention, the proximal portion of the cartridge includes a flange and the hanging is from the flange.

According to some embodiments of the invention, wherein the proximal portion of the cartridge includes a flange and during the hanging, the lateral protrusion extends laterally beyond an outer edge of a portion of the cartridge immediately distal to the flange.

According to some embodiments of the invention, the method further comprises inserting the syringe nest into an automated filling machine.

According to some embodiments of the invention, the aperture is larger than an outer dimension of a barrel of the cartridge by at least 4 mm at least one section thereof.

According to some embodiments of the invention, a cross sectional area of hole is greater than outer cross section by at least 5%.

According to some embodiments of the invention, the lateral projection includes a needle.

According to some embodiments of the invention, an axis of a distal portion of the needle is oriented at an angle of between 15 to 150 degrees to the axis of the cylindrical bore.

According to some embodiments of the invention, an axis of a distal portion of the needle is oriented at an angle of between 80 to 90 degrees to the axis of the cylindrical bore.

According to some embodiments of the invention, the needle is mounted to opening on distal face of bore.

According to some embodiments of the invention, the proximal portion of the cartridge includes a flange and the protrusion extends beyond an edge of the flange.

According to some embodiments of the invention, the method further comprises fixing an orientation of the protrusion around the axis by interlocking the cartridge to an orientation feature on the syringe nest.

According to an aspect of some embodiments of the invention, there is provided a cartridge nest for holding a plurality of cartridges comprising: a syringe nest defining a horizontal array of cartridge mounts each mount for supporting a cartridge, each mount including an aperture sized and shaped to allow a distal portion of a cartridge of the plurality of cartridges to pass through the syringe nest, an support surface shaped to prevent the proximal portion of the cartridge from passing through the aperture such that the cartridge hangs supported on the support surface and the distal portion protruding downward through the aperture and an orientation feature on the cartridge nest sized and shaped to rotationally interlock with the cartridge to fix an angular orientation of the cartridge around its longitudinal axis when the cartridge is hanging from the support surface the orientation feature making the mount not continually rotationally symmetric.

According to some embodiments of the invention, the support surface is shaped to prevent a proximal flange of the cartridge from passing through the aperture.

According to some embodiments of the invention, the each mount is configured for supporting the cartridge by a proximal flange of the cartridge.

According to some embodiments of the invention, the orientation feature is configured to interlock with the proximal flange of the cartridge.

According to some embodiments of the invention, the orientation feature is non-symmetric with respect to 180 degree rotation around the axis of the cartridge.

According to some embodiments of the invention, the array is symmetric to 180 degree rotation around a vertical axis.

According to an aspect of some embodiments of the invention, there is provided a nest for an automatic cartridge filling machine comprising: syringe nest for defining a horizontal array of cartridge mounts, each cartridge mount including: a channel with a non-circular open cross section sized and shaped allow a portion of a barrel of a medicine cartridge to pass through the syringe nest; and an support surface positioned to support the cartridge by preventing a proximal portion of the cartridge from passing through the channel such that the cartridge hangs with the proximal portion supported on the support surface and the portion protruding downward below the channel.

According to some embodiments of the invention, the support surface is positioned to support a proximal flange of the cartridge.

According to some embodiments of the invention, the nest further comprises a plurality of cartridges, each cartridge having a barrel including a cylindrical bore, a protrusion extending laterally beyond the side of the barrel and a flange located proximal to the protrusion and proximal to at least a portion of the barrel; and wherein the open cross section is sized and shaped allow the portion of the barrel and the protrusion to pass through the syringe nest.

According to some embodiments of the invention, the array is symmetric to 180 degree rotation around a vertical axis.

According to an aspect of some embodiments of the invention, there is provided a nest for supporting a plurality of cartridges in an automatic syringe filling machine, each cartridge comprising a barrel having a proximal portion, a distal portion and a lateral protrusion extending from the distal portion comprising: syringe nest for defining a horizontal array of mounts, each mount including: a channel with an open cross section larger than a cross section of the proximal portion of the barrel and sized and shaped allow the distal portion of the barrel to pass therethrough; and an support surface positioned to support the cartridge by preventing a promixal portion of the cartridge from passing through the channel such that the cartridge hangs with the proximal portion supported on the support surface with the distal portion protruding downward below the channel.

According to some embodiments of the invention, each drug cartridge is supported from one of the cartridge mounts with the longitudinal axis directed vertically and the proximal opening facing upward.

According to some embodiments of the invention, the item further comprises: a tub fitting around the syringe nest and protecting the sterility of the nest and the plurality of drug cartridges.

According to some embodiments of the invention, each of the plurality of cartridge mounts includes a support surface positioned to support a proximal flange of one of the plurality of drug cartridges.

According to some embodiments of the invention, the nest further comprises a non-circular apertures in each of the plurality of cartridge mounts; the non-circular aperture sized and shaped allow a distal portion of the each drug cartridge and the needle cap to pass through the syringe nest.

According to some embodiments of the invention, the horizontal array is symmetric to 180 degree rotation around a vertical axis. Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 7A-7C are perspective views of a cartridge with an angled extension mounted off center in accordance with an embodiment of the present invention;

FIGS. 8A-8D are views of cartridges in a syringe nest in accordance with an embodiment of the current invention;

FIG. 9A-9C are a schematic diagrams of an alternative syringe nest in accordance with an embodiment of the present invention;

FIGS. 19A-19C illustrate a further alternative cartridge mount and cartridge in accordance with an embodiment of the current invention.

DESCRIPTION OF SPECIFIC EMBODIMENTS OF THE INVENTION

Figure 1:
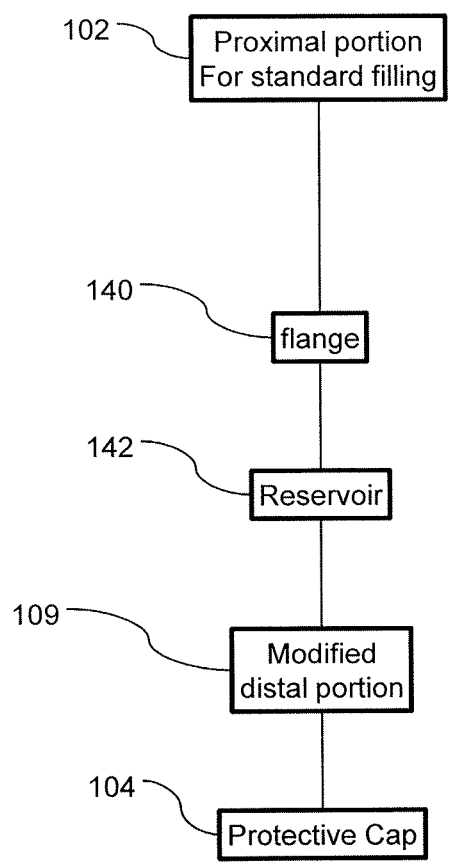
FIG. 1 is a block diagram illustration of a medicine cartridge in accordance with an embodiment of the present invention.

The present invention, in some embodiments thereof, relates to filling of a non-standard syringe and, more particularly, but not exclusively, to automated filling a sterile cartridge with a lateral projection.

Overview

An aspect of some embodiments relates to a method of filling a non-standard medical syringe and/or cartridge. In some embodiments, the cartridge may be filled on a standard filling machine with limited modifications. Optionally the cartridge may be inserted vertically through an aperture in a syringe nest with a distal protrusion of the cartridge extending laterally beyond an edge of a barrel portion of the cartridge. For example, the aperture in the syringe nest may be larger than the barrel section of the cartridge.

An aspect of some embodiments of the current invention relates a syringe nest for filling a non-standard syringe nestpharmaceutical cartridge. For example, the syringe nest may include a non-standard aperture through which a distal part of the cartridge is suspended. Optionally, an aperture may not be round. Alternatively or additionally, an aperture may be larger than a barrel of the cartridge. For example, the aperture may include an opening through which fits the barrel of the cartridge and/or an extension of the opening through which fits a lateral protrusion of the cartridge. In some embodiments, the syringe nest may include a 2D array of such apertures. For example, the array of apertures may be arranged horizontally along the syringe nest. A syringe nest configured to hold a cartridge of a drug discharge device may sometimes be referred to as a cartridge nest.

An aspect of some embodiments of the current invention relates to a mount for a medicine cartridge on a syringe nest, the mount optionally having an orientation feature. For example, an orientation feature may interlock to a cartridge to fix an orientation therefore. For example, the rotational orientation of the cartridge around its longitudinal axis may be fixed. For example, the orientation may be fixed with respect to the syringe nest. Optionally, the orientation of the cartridge may be fixed while it is hanging vertically from a syringe nest. For example, the cartridge may be supported on a support surface of the syringe nest. For example, the cartridge may be supported by a proximal flange of the cartridge. Optionally the orientation element fixes orientation that is not invariant and/or the feature itself is not invariant to rotation of 180 degrees around the vertical axis. For example, the orientation feature may interlock to the proximal flange of the cartridge and/or to a barrel of the cartridge.

In some embodiments, modification may be made in an exchangeable and/or interchangeable part of a syringe-filling machine. The modification may facilitate filling a non-standard cartridge. For example, the modified exchangeable part may include for example a syringe nest, a centering plate, IPC pick and place handling parts, filling needles handling parts, a syringe nest and/or piston stopper distribution parts.

In some embodiments, a non-standard cartridge may include a distal portion with a lateral protrusion. For example, the lateral protrusion may include an angled fluid path. In some embodiments, a proximal portion of the cartridge may be formed for filling like a standard syringe. For example, the proximal portion may include a proximal flange and/or a proximal opening and/or barrel section. In some embodiments, the cartridge includes a drug reservoir with a cylindrical bore. Optionally, the lateral protrusion may protrude laterally from the axis of the bore. For example, the protrusion may extend laterally beyond an outer edge of the barrel section of the reservoir and/or beyond an outer edge of the bore of the reservoir and/or beyond the proximal flange of the reservoir. Optionally, while the cartridge is held in the nest and/or inserted into the nest and/or removed from the nest the lateral projection may project laterally (for example horizontally) beyond an outer edge of the bore of the reservoir and/or beyond the proximal flange of the reservoir.

In some embodiments, a lateral protrusion of a cartridge may include an extension of the fluid reservoir of the cartridge. Optionally, the extension is on a distal portion of the cartridge and/or on a distal end of the cartridge. The extension optionally includes a cap mount and/or the needle tip. For example, the cap mount and/or needle tip may be oriented at an angle ranging between 88 and 92 degrees or between 85 and 95 degrees or between 90 and 100 degrees or between 70 and 110 degrees or between 50 and 130 degrees or between 30 and 150 degrees to the axis of the barrel and/or the bore of a reservoir.

In some embodiments, a dimension of a segment the aperture of a syringe nest and/or a segment of a clear channel including the aperture through which the distal portion of the cartridge moves while being inserted into the aperture may be more than 1 mm and/or more than 3 mm and/or more than 6 mm and/or more than 12 mm and/or more than 24 mm and/or more than 50 mm larger than a corresponding dimension of the cartridge barrel. For example, the aperture may include an expanded segment where the edge of the aperture is distanced laterally from the edge of the barrel when the barrel is hung on the syringe nest. For example, the expanded segment may surround between 1 to 5% and/or between 5 to 10% and/or between 10 to 20% and/or between 20 to 30% and/or more than 30% of the barrel. For example, the edge of the aperture of the extended section may extend be more than 1 mm and/or more than 3 mm and/or more than 6 mm and/or more than 12 mm and/or more than 24 mm and/or more than 50 mm larger than a corresponding portion of the cartridge (for example a portion of the cartridge horizontally to the extended edge) while the cartridge is hanging from the syringe nest. For example the cross sectional area of the free channel and/or the aperture may be between 5% to 10% and/or between 10% to 20% and/or between 20% to 50% and/or more than 50% larger than the cross section of a proximal section of the barrel (for example the section of the barrel just distal to the flange and/or the portion of the barrel inside the channel and/or just inside the aperture while the cartridge is hanging from the support surface). In some embodiments, an aperture in a syringe nest and/or an open channel through the nest may include a large opening fitting the barrel and/or flange of the cartridge and/or a narrow extension fitting a lateral projection of the cartridge.

In some embodiments, an orientation element may include a protrusion on the syringe nest that interferes with rotation of part of the cartridge. For example, the protrusion may interfere with rotation of a proximal flange of the cartridge. For example, the flange may have a cut out and/or a flat portion that contacts the protrusion. A protrusion may include a pin. For example, a pin may fit into an aperture on the cartridge (for example on the proximal flange). For example, the pin may secure the flange to the syringe nest at a fixed orientation. Alternatively or additionally, the orientation element may include an indentation and/or a hole fitting to a coupling of the cartridge. For example, the flange of the cartridge may fit into indentation with a non-rotational shape. Alternatively or additionally, a pin protruding from the cartridge (for example from the flange) may fit into a hole in the nest (for example in a syringe nest thereof) fixing an orientation of the cartridge to the nest. Alternatively or additionally, an outer shape of the barrel of the cartridge may be non-circular and may fit into an aperture in the syringe nest in a specific orientation.

In some embodiments, an orientation element may include a bevel and/or chamfer. For example, if a cartridge is inserted not at the desired orientation, the bevel and/or chamfer may guide the cartridge to the desired orientation. Optionally an orientation will be fixed within a defined tolerance. For example, the rotational tolerance may range less than 3 degrees and/or less than 8 degrees and/or less than 15 degrees and/or less than 30 degrees. An orientation element may preserve orientation of a cartridge in a cartridge nest during storage and/or transport and/or when the cartridge is being filled. For example, the orientation element may prevent the cartridge from changing orientation will the syringe nest is being moved during the filling process.

In some embodiments, a syringe nest may hold an array of cartridges. For example, cartridge mounts and/or apertures in a syringe nest may be arranged in a horizontal array. Optionally the cartridges may be held in a horizontal array. For example, each cartridge in the array may be supported at the same height. In some embodiments, an array of apertures in a syringe nest may be arranged according to requirements of a syringe-filling machine. Optionally, columns of cartridges are arranged without overlap of a portion of one column into the center of gravity of another column. For example, avoiding overlap may enable a lifting bar to push up one column of containers from underneath the nest without disturbing the neighboring column. For example, a machine may lift the entire column from below with a flat lifting bar.

In some embodiments, the array of cartridges may be invariant over a 180-degree rotation. For example, filling the cartridges in a syringe nest may be independent of which way the nest is inserted.

In some embodiments, an array of syringe mounts may be arranged in a plurality of the columns and/or rows. The syringe mounts may be included on a syringe nest. Subsequent rows and/or columns may be separated by a single separation distance. Optionally all and/or a plurality of the columns and/or rows may be staggered by a single offset distance (optionally of alternating direction). For example the row and/or column separation (for example center to center) distance may range between 3 to 5 mm and/or between 5 to 15 mm and/or between 15 to 50 mm and/or between 50 to 100 mm and/or between 100 to 200 mm. For example, the offset distance may range between 0 to 4 mm and/or between 4 to 15 mm and/or between 15 to 45 mm.

In some embodiments, the cartridge may be held in and/or inserted into and/or removed from a syringe nest with the axis of the reservoir bore substantially vertical. For example, the axis may be at an angle of less than 2 degrees to vertical and/or less than 7 degrees and/or less than 15 degrees. Optionally, inserting the cartridge into the nest may include inserting a distal portion of the cartridge along a channel passing through an aperture in a syringe nest of the nest. For example, the channel may have an opening large enough to pass the distal portion therethrough, but small enough to prevent passage of a proximal portion and/or the proximal flange therethrough. Optionally, holding the cartridge may include hanging the cartridge from a proximal flange thereof with the distal end of the cartridge facing downward. For example, the flange may be supported by a support surface of the nest. Optionally, that support surface may form a part of the edge of the channel.

In some embodiments, the proximal portion of a cartridge may be standard enough to fit a standard and/or minimally modified filling machine. For example, the modified syringe may fit into a modified nest, which fits into a conventional filling machine. Optionally, the cartridge is configured to be pre-filled with a drug using standard syringe filling equipment.

In some embodiments, an extension of a cartridge includes a syringe tip, for example, having a built in needle and/or a needle mount and/or a mount for a protective cap at an angle to the axis of the barrel of the cartridge. Optionally, the distal side of the cartridge is balanced enough to hang substantially vertically in a nest. For example, the cartridge may hang with a longitudinal axis of a bore thereof at an angle between 0-1 degree and/or 1-2 degrees and/or 2 to 3 degrees and/or 3 to 5 degrees. Optionally, part of the distal end may bulge and/or protrude outside the cross section of the barrel of the cartridge. The bulge and/or protrusion is optionally small enough to fit in an optionally modified cartridge nest. For example, the length of a bulge and/or protrusion may be limited to 1-4 mm and/or 4-10 mm and/or 10-20 mm and/or 20 to 40 mm.

In some embodiments, a cartridge may include a medicine reservoir for an auto-injector. Optionally the reservoir may be pre-filled in a sterile aseptic environment using standard equipment for filling syringes. Filling is optionally prior to insertion into the injector. Optionally, the injector itself need not be sterile and/or not as strictly sterile as the cartridge.

In some embodiments, a bent fluid path may be produced by plastically bending a hollow tube. The tube is optionally cleaned after bending (for example to remove any particles produced during the bending). Optionally a superstructure is added to the tube.

For example, the superstructure may be molded around the tube (for example using techniques of insert molding). For example, then superstructure may be formed of plastic and/or a resin. Optionally, a portion of the tube may be exposed. For example, one or both ends of the tube may protrude from the superstructure. Optionally or additionally, the superstructure may include a mount for a sterility protecting needle cover.

In some embodiments, the extension is associated with a reservoir. For example, the extension may be integrally formed with a reservoir and/or attached to a reservoir. For example, the reservoir and extension together may be included in a medicine cartridge (e.g. a prefilled syringe and/or a cartridge for a drug delivery device). Optionally, the entire cartridge including the reservoir and/or the extension and/or the cover is sterilized. For example, the cartridge is sterilized as a sealed unit. Optionally the cartridge may be filled and sealed with a stopper. For example, the cartridge may be configured for filling in a conventional and/or minimally modified syringe filling machine.

In some embodiments, a lateral protrusion of a cartridge may be rigidly connected to the reservoir. For example, a perpendicular force of 5 N or less (for example between 0 to 2 N and/or between 2 to 5 N) on the extension (for example at the base of the needle and/or at the bent portion of the extension and/or at a needle mount of the extension) may change the angle of the distal portion of an axis of the cartridge by less than 2 degrees. In some embodiments, the extension may protrude beyond the profile of the walls of the reservoir.

In some embodiments, the fluid path may be mounted eccentrically and/or bend around to cross a center line of the reservoir. For example, the path may be configured to balance its weight. For example, the weight may be balanced so that the syringe hangs substantially vertically in a nest of a filling machine and or to facilitate opining the cartridge around its axis, for example, in order to test for particles.

The design of the flow path may reduce the length of a protrusion from the profile of the reservoir (for example to reduce the size of a hole in the nest). For example, protrusions (for example including a needle and/or needle cap) may be limited to less than 10 mm and/or less than 25 mm and/or less than 40 mm from an outer edge of the projection of the cylindrical walls of the reservoir and/or of the outer wall of the reservoir and/or less than less than 25 mm and/or less than 35 mm and/or less than 60 mm in a direction perpendicular to the longitudinal axis of the cylindrical reservoir.

In some embodiments a syringe nest may be used in an automatic filling machine. Alternatively or additionally, the nest may be used when hand filling a cartridge.

DETAILED EMBODIMENTS

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Cartridges

FIG. 1 is a block diagram of a cartridge with a modified distal portion in accordance with an embodiment of the current invention. Optionally, a distal portion 109 of the cartridge may have features that are customized for use in a drug delivery device. In some embodiments, an injector cartridge may have a proximal portion 102 that is similar to a conventional syringe. For example, a proximal portion may include a flange 140 and a proximal opening. Optionally the proximal portion is configured for handling by a conventional and/or minimally modified automated syringe filling machine. For example, proximal portion 102 may include modifications that are designed to facilitate connection of the cartridge to a drug delivery device and/or filling the cartridge with a drug in an automatic filling machine. For example, proximal portion 102 may include modifications adapted for orienting distal portion 109 in the filling machine.

In some embodiments, distal portion 109 of the cartridge may include modifications for an automated drug delivery device. For example, distal portion 109 may include a lateral protrusion. For example, the lateral protrusion may include an angled extension and/or an angled needle. Optionally, distal portion 109 may include and/or be covered and/or be protected by a cap 104. For example, a needle may be covered with a needle cap. Distal portion 109 may be designed to reduce a length of the protrusion. For example, an angled extension is optionally offset away from an axis of the cartridge and/or set back to reduce the size of a protrusion. For example, the extension may be offset in one direction and/or bent back toward an opposite direction.

In some embodiments, a cartridge may include a reservoir 142. Reservoir 142 optionally includes an approximately cylindrical cavity (e.g. a bore). For example, the cavity may fit a syringe plunger. Optionally, the bore may include a lead in bevel and/or chamfer. Optionally, a proximal section of the reservoir may have the form of a standard syringe including for example a flange 140 and/or a barrel. For example, flange 140 may be located at the proximal end of the barrel section of the cartridge. For example, flange 140 may be configured to support the cartridge on a syringe nest of the filling machine. Flange 140 optionally includes modifications, for example for helping to orient the cartridge during filling. Optionally, a part of distal portion 109 may protrude laterally beyond an outer edge of the bore and/or of the barrel section and/or flange 140 of the cartridge.

In some embodiments, a protrusion may be balanced. For example, reducing a size of a protrusion may facilitate fitting of one or more cartridges into a nest of a filling machine. For example, balancing a protrusion may improve the angle at which a cartridge hangs in a filling next and/or may facilitate automatic handling of the cartridge.

Optionally the sterility of the cartridge and/or the pharmaceutical substance may be preserved and/or guaranteed for lengthy periods of time.

In some embodiment, the cartridge and/or the needle and/or the needle cap may be sterilized. Optionally they may be assembled and then sterilized as a single unit. Alternatively or additionally, the cartridge and/or the extension may be sterilized separately from the needle and/or the needle cap. Optionally, the cartridge and/or the extension may be sterilized while supported on a syringe nest and/or while enclosed in a closed and/or sealed tub.

Example of Packing a Syringe Nest

Figure 2:
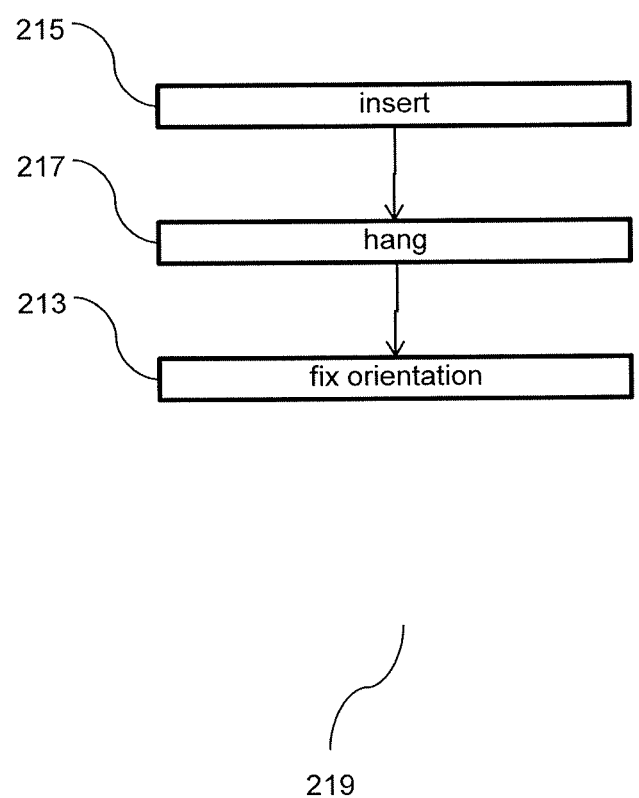
FIG. 2 is a flow chart illustration of a method packing a syringe nest in accordance with an embodiment of the present invention.

FIG. 2 is a flow chart illustration of a method of packing 219 a syringe nest in accordance with an embodiment of the current invention. In some embodiments, a distal portion of a cartridge may be inserted 215 through a channel including an aperture in a syringe nest. Optionally the cartridge includes a lateral protrusion. For example, the protrusion may fit through the channel in a limited range of orientation. For example, the cartridge may be inserted 215 with a longitudinal axis vertically downward and the laterally protrusion oriented to fit through an extension of the aperture. Optionally, the orientation of the cartridge is fixed 213 with respect to a protective packaging and/or a syringe nest thereof. For example, fixing 213 the orientation of the cartridge with respect to the syringe nest may facilitate subsequent removal of the cartridge from the syringe nest.

In some embodiments, one or more cartridges are packed 219 into a nest, for example, for storage and/or handling. For example, cartridges may be hung 217 in the nest with a proximal end facing upward, a distal end downward and/or a longitudinal axis directed vertically. Optionally, a cartridge may be sensitive to orientation around a longitudinal axis thereof. For example, the cartridge may fit into and/or be removed from the nest in a limited range of orientations and/or handling of the cartridge may be dependent on an orientation. In some cases, it may be desirable to keep a cartridge properly oriented. In some cases, storage transport and/or handling of the nest may tend to disorient a cartridge. Optionally, when a cartridge is packed into a nest, its orientation around its longitudinal axis may be fixed 213 with respect to a syringe nest of the nest.

In some embodiments, one or more cartridges may be packed 219 into a nest. Each cartridge is optionally hung 217 from a mount. For example, a proximal flange of the cartridge may rest on a support surface of the mount while a distal portion of the cartridge may hang 217 below the mount. Optionally, a proximal portion of a barrel of the cartridge hangs 217 through a channel in the mount. In some embodiments, an array of mounts is arranged on a syringe nest. For example, the mounts may be arranged in a 2D horizontal array along the syringe nest. Optionally, the channel of each mount includes an aperture of the syringe nest.

Exemplary Syringe Nest

Figure 3:
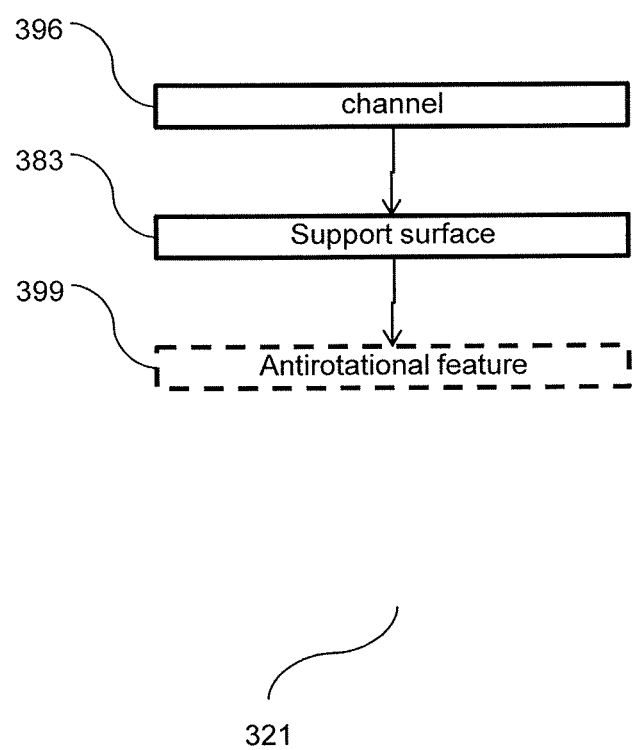
FIG. 3 is a block diagram illustration of a syringe nest in accordance with an embodiment of the present invention.

FIG. 3 is a block diagram illustration of a syringe nest in accordance with an embodiment of the present invention. Optionally a syringe nest includes a horizontal array 321 of cartridge mounts. For example, each mount may include a channel 396 having an open cross section that is larger than a barrel of the cartridge. Optionally, the open cross section of channel 396 may be non-circular.

In some embodiments, a cartridge mount will include an orientation feature 399 (for example, the feature may fix an orientation of a cartridge with respect to the mount and/or may impede rotation of the cartridge and/or may sometimes be referred to as an anti-rotation feature). For example, orientation feature 399 may inhibit rotation of the cartridge around its axis while the cartridge is supported on the syringe nest.

In some embodiments, a syringe mount may include a support surface 383. Alternatively or additionally, a barrel of the cartridge may have a tapered portion that is supported on a support surface. Optionally the support surface may be horizontal. For example, support surface 383 may include a surface of a collar. Optionally the collar defines a channel. Alternatively or additionally, support surface 383 may include portion of the upper surface of the syringe nest. For example, a portion of a proximal flange of the cartridge may rest on the support surface. Alternatively or additionally, the cartridge mount may include an inward protrusion in the sides of channel 396. The protrusion may support the flange of the cartridge and/or fit into a groove in the cartridge and/or support the top of the groove. Alternatively or additionally, the support surface may be sloped and/or vertical. For example, a tapered portion of a barrel of a cartridge may be supported by a vertical side of channel 396.

Example of a Syringe Nest

Figure 4A:
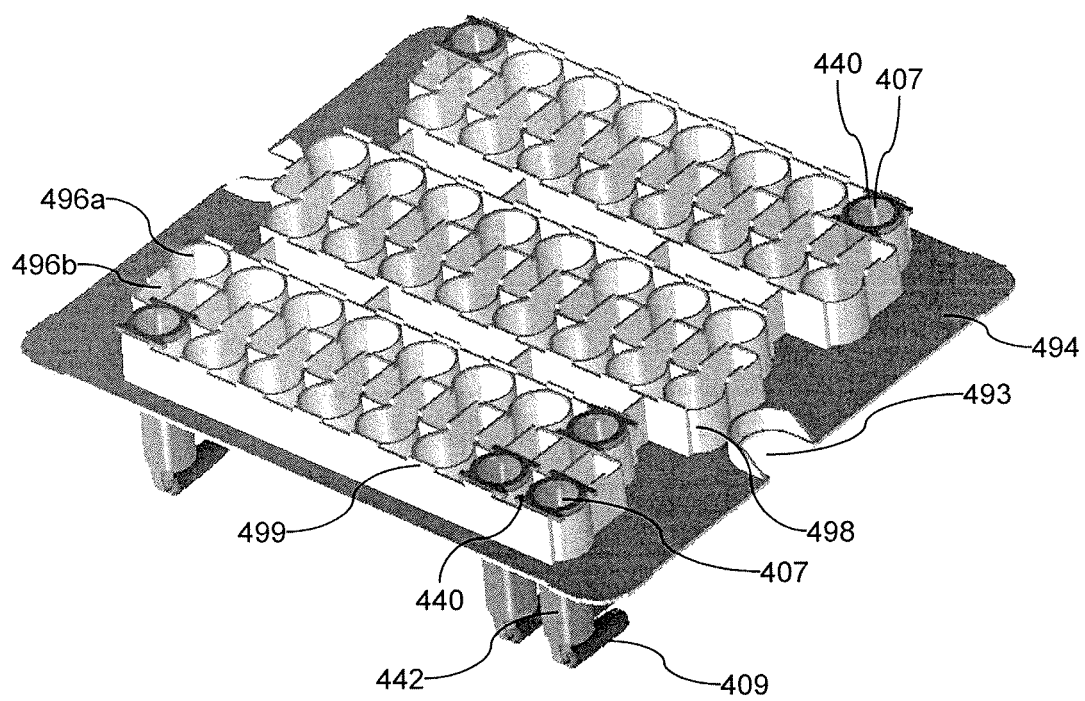
FIGS. 4A-4B are perspective views of a syringe nest in accordance with an embodiment of the present invention.
Figure 4B:
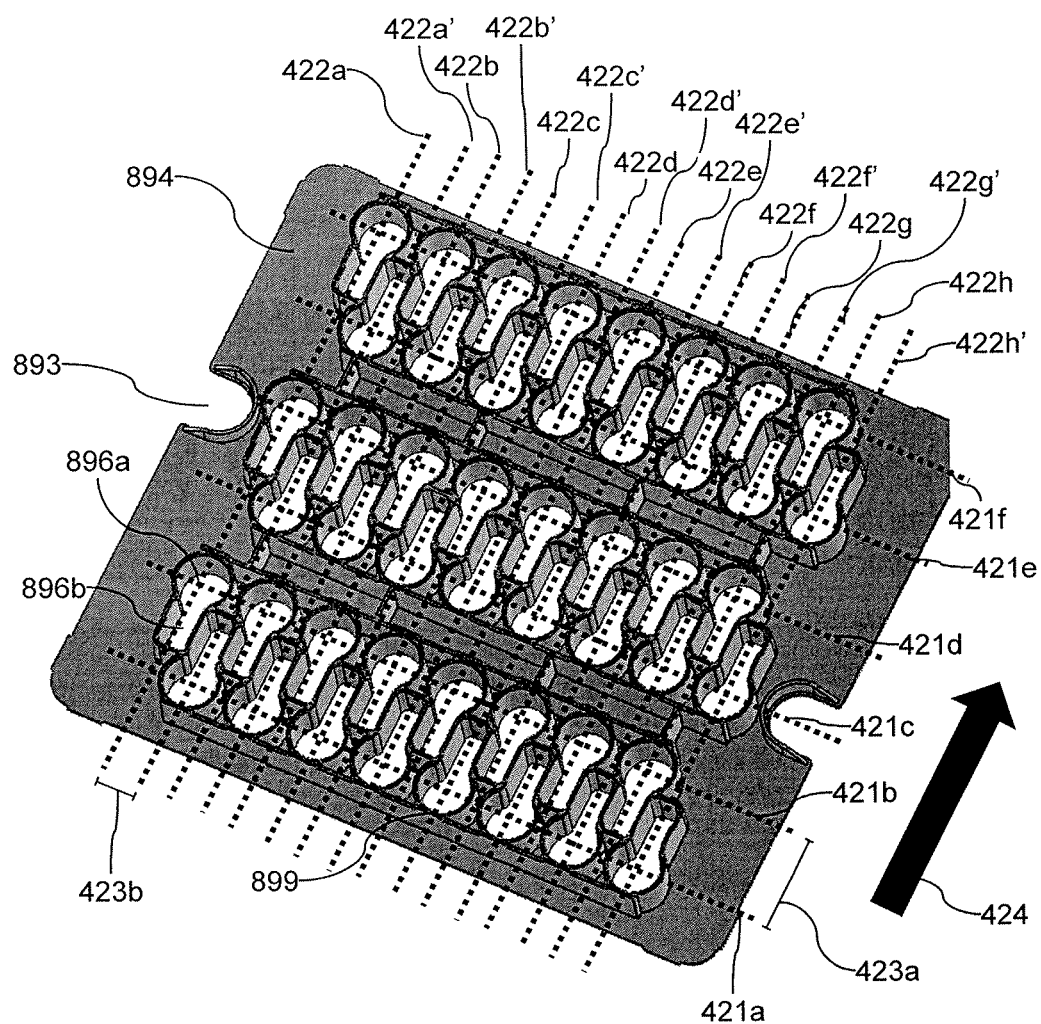

FIGS. 4A-4B are perspective views of a syringe nest in accordance with an embodiment of the present invention. The exemplary syringe nest includes 48 non-circular apertures. Optionally, each aperture is sized and/or shaped to allow a distal portion of a cartridge to pass therethrough. Optionally, a collar 498 surrounds each aperture. Optionally collar 498 includes an upper surface that supports a flange of the cartridge. Optionally, each aperture includes a round opening and an elongated thin extension. Optionally the protrusion and/or the extension extend laterally beyond the flange of the cartridge and/or beyond the support surface of the mount and/or beyond an outer edge of a barrel of the cartridge and/or beyond an edge of a bore of the cartridge.

In some embodiments, a syringe nest includes six columns and eight rows of cartridge mounts. Optionally, each mount includes a main aperture 496a and an extension 496b. For example, main aperture 496a is sized and shaped to allow the barrel of the cartridge to fit therethrough and/or an extension aperture 496b is sized and shaped to allow a distal extension of the cartridge to fit therethrough. Optionally, each mount includes a collar 498 raised from the surface of a syringe nest 494. For example, the inner walls of collar 498 define a channel through the syringe nest. Optionally, the upper surface of the collar 498 forms a support surface.

In the exemplary illustration of FIG. 4A, six cartridges are shown hanging from the syringe nest. For example, each cartridge includes a flange 440 that is supported on a top surface of a collar 498. An optional barrel 442 hangs vertically (e.g. with a long axis barrel 442 directed vertically) downward from flange 440. For example, a proximal portion of barrel 442 is connected to flange 440. For example, the proximal portion of barrel 442 hangs inside main aperture 496a while a distal portion of barrel 442 hangs under main aperture 496a. Optionally the distal portion of barrel 442 includes and/or is attached to a lateral protrusion 409. Optionally, lateral protrusion 409 is lined up with and/or underlies extension aperture 496b. While the exemplary illustration of FIG. 4A includes six cartridges hanging from six mounts and 42 empty mounts, a syringe nest may be supplied to a medicine packager with a different number of cartridges. For example, a nest may be supplied completely full (e.g. with a cartridge hanging from each mount e.g. in the exemplary illustration of FIG. 4A with 48 cartridge).

In some embodiments, the cartridge may be removed from the syringe nest by lifting vertically. For example, when a cartridge is lifted vertically, protrusion 409 fits and/or passes through of the syringe nest through extension aperture 496b while barrel 442 fits and/or passes through main aperture 496a.

In some embodiments, an orientation element 499 fixes a rotational orientation of the cartridge around the axis of barrel 442. For example, element 499 includes a flat protrusion that contacts a flat surface of flange 440 fixing the orientation of the cartridge. For example, the orientation is fixed such that protrusion 409 underlies extension aperture 496a.

In some embodiments, while a cartridge is supported on the syringe nest an opening 407 to a cylindrical bore of barrel 442 is pointed upward. For example, this may facilitate filling of the bore. Optionally, opening 407 includes a lead in chamfer. For example, the lead in chamfer may make it easier to insert a plunger seal into opening 407.

In some embodiments, cartridge mounts in a syringe nest may be interleaved. For example, in the exemplary embodiment of FIG. 4A, extension apertures 496b are interleaved.

For example, between every two extensions apertures 496b of one column, there intervenes an extension aperture 496b of the neighboring column. Optionally, interleaving is adapted such that the center of gravity of a column is not interrupted. Optionally the syringe nest includes handles 493. For example, handles 493 may be used to orient and/or align syringe nest 494.

FIG. 4B illustrates an array of cartridge mounts on a syringe nest in accordance with an embodiment of the current invention. Optionally the six columns of mounts are labeled 421a, 421b, 421c, 421d, 421e, 421f. Dotted lines illustrate the center of mass of a cartridge hanging from a mount in each column 421a-421f. For example, the center of gravity of each cartridge in the exemplary illustration underlies the barrel of the cartridge and/or main aperture 496a of each mount. A line connected the centers of gravity of the cartridges of a single column 421a-421f optionally is not interrupted by any part of another column 421a-421f. For example, this facilitates lifting up an entire column 421a-421f of cartridges from underneath for example with a lifting bar.

In FIG. 4B some of the rows 422a-422h' are marked with dashed lines. Optionally, the eight rows of cartridge mounts in each column of are staggered. For example, staggering may include offsetting row 422a from row 422a' by a row to row offset distance 423b.

In some embodiments, the column to column separation distance 423a is equal between all adjacent columns. For example, this may facilitate filling in some filling machines that progress from column to column a constant fixed distance. Optionally the separation distance between all rows of a single column (e.g. from 422a to 422b to 422c to 422d to 422e to 422f to 422g to 422h) are all equal. For example, this may facilitate filling by some filling machines, which have a fixed and/or an equal distance between filling tubes. Alternatively or additionally, the offsets of respective rows of each set of subsequent columns (e.g. from 422a to 422a' and/or 422b to 422b' and/or 422c to 422c' and/or 422d to 422d' and/or 422e to 422e' and/or 422f to 422f' and/or 422g to 422g' and/or 422h to 422h') are all equal. Alternatively or additionally, the respective offset of subsequent sets columns are in opposite directions. In some embodiments, a syringe nest is invariant to 180 degree rotation. For example, rotating the syringe nest of FIGS. 4A and/or 4B by 180 degrees results in the exact same positioning and/or orientation of mounts, rows, columns and/or handles and/or cartridges. Alternatively or additionally, in some embodiments only the centers of gravity of rows and/or columns may be invariant to 180 degree rotation.

In some embodiments, a syringe nest may be designed for a specific direction of filling. For example the direction of filling of the exemplary syringe nest of FIG. 4B is illustrated by an arrow 424. For example, first column 421a is filled and then column 421b and then column 421c and then column 421d and then column 421e and then column 421f. Optionally the syringe nest may be rotated 180 degrees and filled in exactly the opposite direction. In some embodiments, a syringe nest may be filled in a direction that is perpendicular (after a 90 degree rotation). Optionally to fill the syringe nest after a rotation of 90 degrees may require readjusted the filling machine and/or changing exchangeable parts.

Example of Packing a Cartridge Nest

Figure 5A:
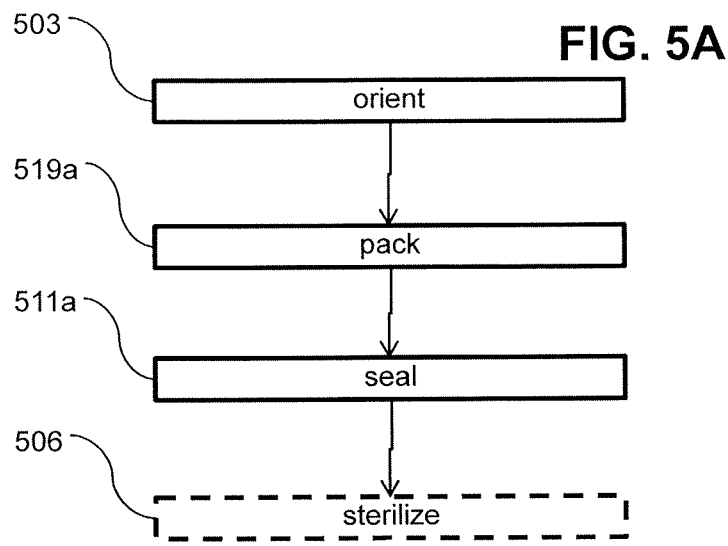
FIGS. 5A and 5B are flow chart illustrations of packing an array of cartridges during for example manufacture and/or filling in accordance with an embodiment of the present invention.
Figure 5B:
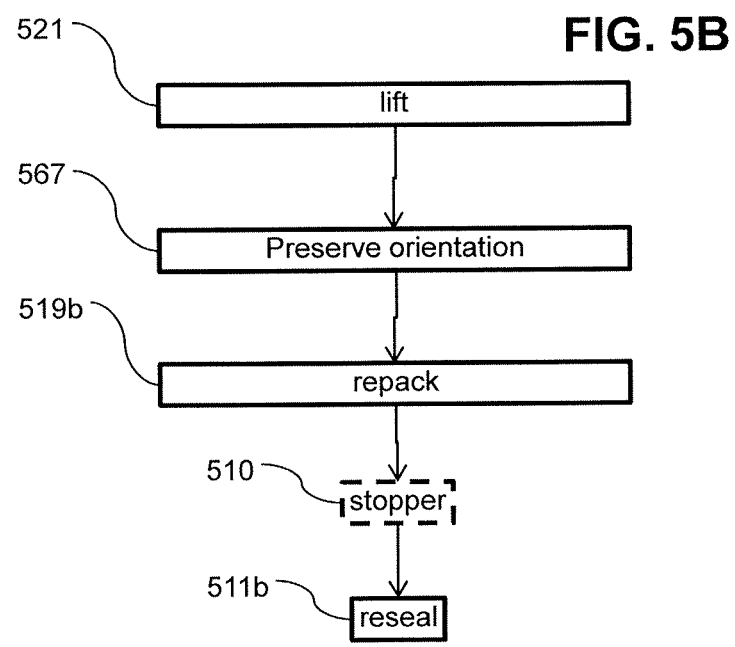

FIGS. 5A and 5B are flow chart illustrations of packing an array of cartridges during for example manufacture and/or filling in accordance with an embodiment of the present invention.

FIG. 5A illustrates packing a nest of cartridges with cartridges that are initially non-oriented. For example, after manufacture the cartridges may be non-oriented. For example, a device packer may orient 503 each cartridge and/or each groups of cartridges and pack 519a them into a nest and then seal 511a the nest. Optionally the sealed nest may be sterilized 506.

FIG. 5B illustrates packing a nest of cartridges with cartridges that are initially oriented. For example, a drug packager may receive a nest full of cartridges oriented and/or packed into the nest. Optionally, the drug packager may fill the cartridges with a pharmaceutical in a filling machine. For example, a machine may lift 521 one or more cartridges out of the nest, for example in order to weight them. While lifting 521 a cartridge, the machine may preserve 567 the orientation of the cartridges. For example, a lifting bar and/or a griper and/or a weighing cell may be modified to preserve 567 orientation of the cartridge during handling. The cartridges may, for example, be repacked 519b into the nest. Optionally the repacked cartridges are stoppered 510 and/or the nest is resealed 511b.

Example of Filling a Cartridge

Figure 6:
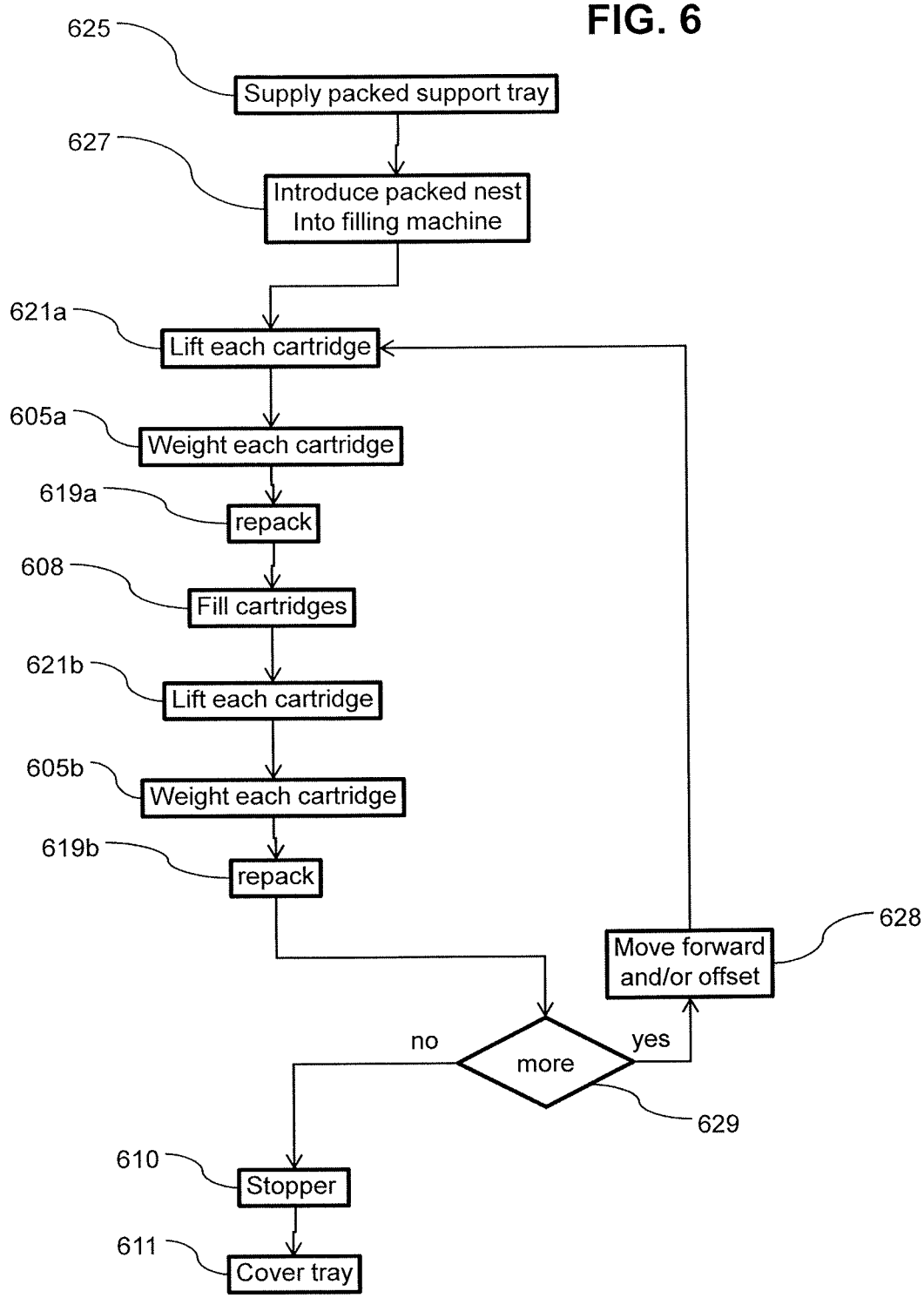
FIG. 6 is a flow chart illustration of a method of filling a cartridge in accordance with an embodiment of the present invention.

FIG. 6 is a flow chart illustration of a method of filling a syringe in accordance with an embodiment of the current invention. In some embodiments, a sterile fully packed nest is supplied 625 to a drug packager from a device packer. The nest is unsealed and/or introduced 627 into the filling machine.

In some embodiments, cartridges may be processed while in the syringe nest. For example, the syringe nest of the nest may be used to for handling the cartridges during filling. For example, the cartridges may be packed in the syringe nest with a proximal opening of the reservoir facing upward. The syringe nest is optionally positioned with a row of cartridges under a set of filling tubes and a column of cartridges is filled. For example, for the syringe nest of FIGS. 4A and 4B column 421a may be positioned under eight filling tubes that fill 608 the eight cartridges together while they are hanging from the syringe nest. Optionally the syringe nest is then moved 628 forward (opposite the direction of arrow 424) and offset to the right to position column 421b under the filling tubes. The process optionally continues moving 628 forward and offsetting in alternating direction to fill columns 421a to 421f.

In some embodiments, a cartridge may be removed from the syringe nest and later replaced. For example, before filling, each empty cartridge may be lifted 621a and/or weighed 605a in a process control (IPC) station.

In some embodiments, lifting 621a a single cartridge is a multi-step process. Optionally, an individual cartridge is removed from the nest using a gripper to grab a flange and/or the body of the cartridge. Optionally, the flange and/or the body of the cartridge may be made accessible by raising the cartridge slightly from below. For example, a column of cartridges may be positioned over a lifting bar. The bar is optionally raised pushing upward on the center of gravity of the cartridges, raising them slightly from the syringe nest. A gripper optionally grasps a single raised cartridge. In some embodiments, the gripper is used to place a single cartridge onto a weighing cell wherein the cartridge is weighed 605a. In some embodiments, the gripper is used to repack 619a the cartridge back into the nest before filling 608. Alternatively or additionally, the cartridge is filled before being repacked into the nest (for example filling may occur in the IPC station).

In some embodiments the nest is designed so that the centers of gravities of all the cartridges in a column are lined up without any interfering element between them. Alternatively, a lifting bar may be modified to include protrusions that raise the intended cartridges and recessed zones, where intervening cartridges are not disturbed. In some embodiments, a gripper and/or a weighing cell may be modified to fit a cartridge with a modified distal section. In some embodiments, a gripper and/or a weighing cell may be modified to preserve orientation of a cartridge during handling such that the cartridge is repacked in the nest in the same orientation that it had when it was lifted and/or reoriented in a predetermined way.

In some embodiments, a cartridge may be lifted 621b and/or weighed 605b and/or repacked 619b into the nest after filling 608. Alternatively or additionally, for example when the empty cartridge is not repacked 619a to the nest before filling, the cartridge may lifted 619a once and/or weighted empty 605a and/or filled 608 and/or weighted full 605b and/or repacked 619b once.

In some embodiments, further operations and/or alternative orders of operation of a filling machine are possible within the spirit of the current invention. For example, a custom cartridge may be filled in a continuous line filling machine. For example, a continuous line filling machine may include a orienting station orient an empty cartridge as it enters the machine and/or as it approaches a filling station and/or as it approaches an IPC station.

In some embodiment, a cartridge may undergo further inspection before, during and/or after filling. For example, a full cartridge may be testing for particle content. Optional testing for particle content may be performed after stoppering. For example, a stoppered cartridge may be spun and/or braked and/or centrifuged. Optionally, the cartridge may be configured to facilitate inspection. For example, a protrusion may be balanced (for example by offsetting an extension from the center of the cartridge and/or by including a counter balance) to facilitate spinning. For example, an extension and/or cap may be configured to withstand G forces of inspection processes (for example the cap may be offset towards the center of the cartridge to balance G forces so that it is not pulled off during spinning and/or an extension may be rigid enough to avoid bending during spinning and/or braking). Optionally, an inspection station may be configured to properly orient a cartridge during inspection processes and/or to reorient the cartridge after inspection for repacking into a nest and/or after inspection the cartridge may be packed in a package that does not require specific orientation.

In some embodiments, after filling 608 and/or weighting 605a, 604b (e.g. when there are no more 629 empty cartridges), the cartridges are stoppered 610. For example, while a cartridge is in the syringe nest, it is positioned under a stoppering tube (for example column by column and/or cartridge by cartridge and/or pair by pair and/or four by four etc.). For example, a stoppering tube may first seal to a proximal surface of the cartridge and/or apply a vacuum to the proximal opening of the cartridge. Optionally, under vacuum a stopper (e.g. a plunger seal) is placed into the proximal opening of the cartridge. The vacuum may optionally be released. Optionally air pressure then drives the stopper into the bore of the cartridge reservoir. For example, the stopper may enter until it contacts the proximal end of the portion of the cartridge that is filled with the drug. Additionally or alternatively, the reservoir is filled 608 and/or stoppered 610 without using a vacuum. For example, a venting tube may be inserted between an outer edge of the stopper and the inner wall of the reservoir during stoppering

610. The venting tube optionally allows air to escape as the stopper in inserted into the reservoir.

In some embodiments, the cartridge may be filled 608. For example, the cartridge may be filled 608 with a drug in a standard and/or a minimally modified aseptic filling machine. Optionally the cartridge may be filled while the needle in place on the cartridge and/or with a needle cap attached. Optionally the drug may be a liquid. Optionally a drug is introduced into an internal cavity of the reservoir (for example a bore thereof) through a proximal opening of the cartridge. Optionally the proximal opening is stoppered 610. For example, stoppering may include sealing the proximal opening of the cartridge with a plunger seal for example after filling. Optionally after filling 608 and/or stoppering 610, the nest may be covered 611. For example, covering 611 may include sealing the nest with a vacuum bag and/or covering a top of the nest.

In some embodiments, the cartridge is inserted into a drug discharge device, for example an injector device. Optionally, cartridge is loaded into the injector in a filled and/or sterile state. The loading action is typically carried out with the needle cap in place. For example, the injector device may not be guaranteed to be sterile to the same degree as the contents of the cartridge and/or the needle. The injector device with the cartridge is optionally supplied to the patient. The needle cap may optionally be removed for use by the patient and/or a medical helper and/or a doctor and/or a pharmacist.

In some embodiments, a cartridge may be installed to the delivery device before assembly of the device and/or before shipping the device to a retailer and/or a health provider and/or a user. Alternatively or additionally, the cartridge may be installed into the drug delivery device by a user, for example a health provider (for example a nurse and/or a pharmacist and/or a doctor and/or a health aid) and/or a subject of the injection (e.g. a patient receiving the drug) and/or a caretaker.

In some embodiments, an assembled injector, with the cartridge installed, may be supplied to a user. Optionally as supplied to the user, the cartridge and/or extension and/or the needle may be sterile and/or covered with the protective cap. Optionally, the injector may have a needle shield latch. For example, while the needle cap is in place the needle shield latch may be in an open position, allowing the access to the needle cap. For example, when the needle shield latch is in the open position there may be space for the cap and/or a cap remover to protrude out of the injector. For example, in the open position, the needle shield latch may retract. In some embodiments the needle shield latch may pivot and/or slide from one position and/or state to another. Alternatively or additionally, the cartridge and/or the injector may be supplied to the user separately and/or may be assembled by the user.

Exemplary Cartridge with Lateral Protrusion

Figure 7B:
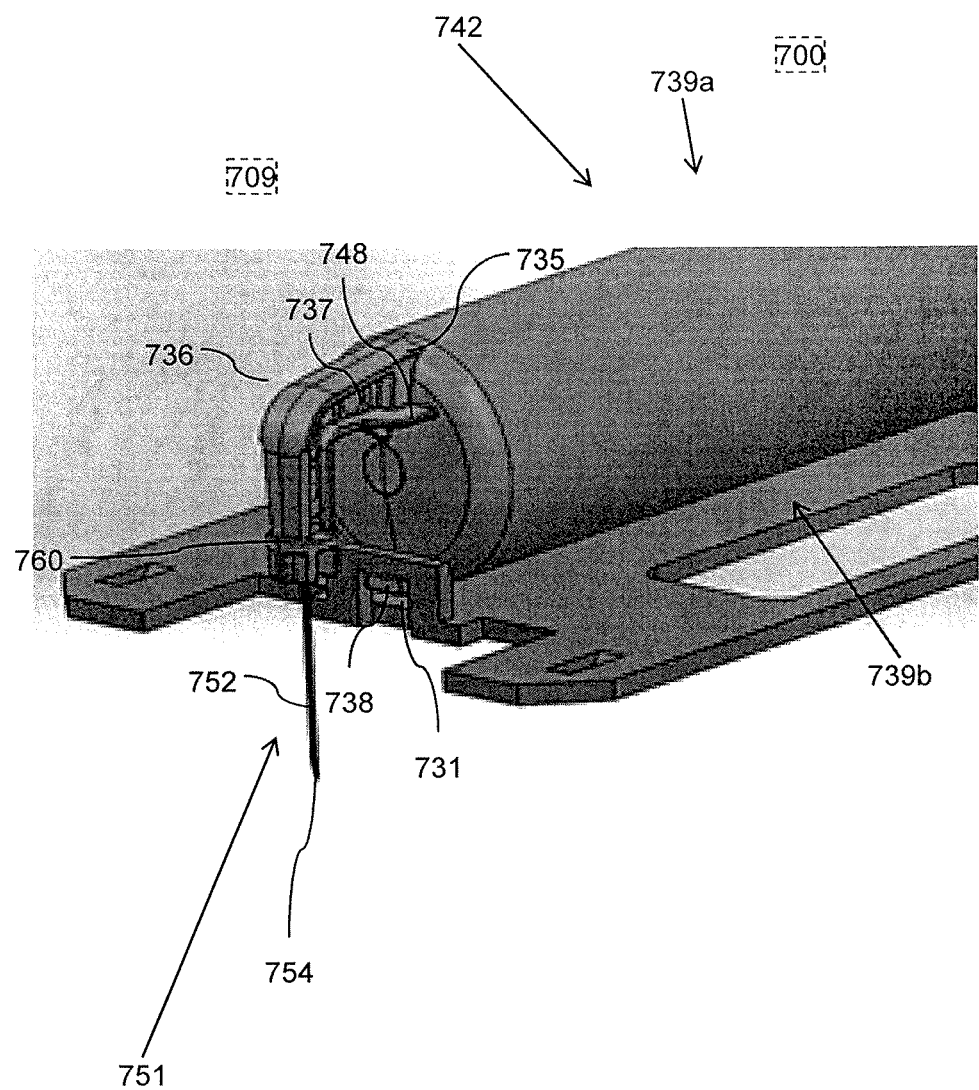
Figure 7C:
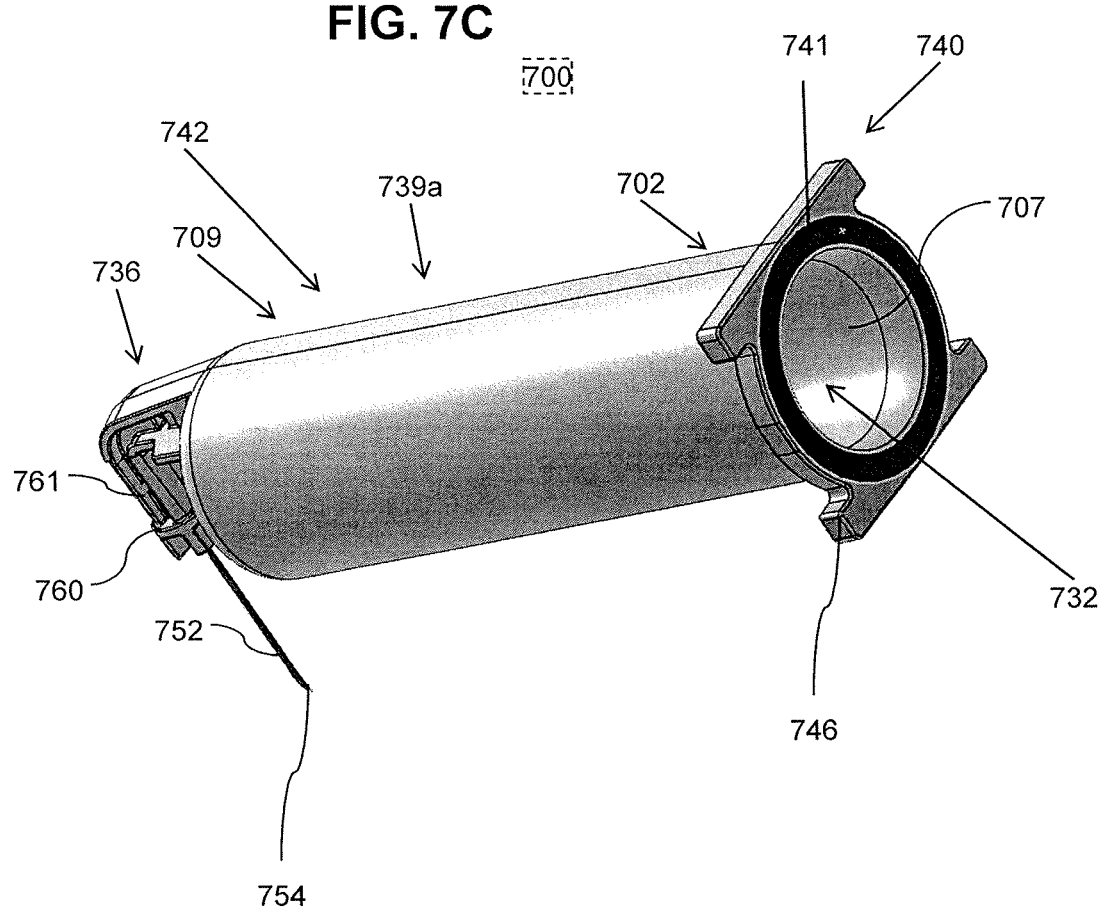

FIGS. 7A, 7B and 7C are perspective views of a cartridge in accordance with an embodiment of the current invention. Optionally, the cartridge is in the form a modified cartridge 700 including, for example, a reservoir for a drug delivery device. Optionally, cartridge 700 includes an angled extension 736. For example, extension 736 includes a bent arm mount off the center axis 758 of a cylindrical cavity 732 of a barrel 742. Optionally a fluid path connects to the cavity of the barrel and/or passes through extension 736. Optionally the bent arm is molded and/or formed in one piece with barrel 742. For example, extension 736 protrudes laterally (in the ventral direction) from a distal end 709 of barrel 742. Optionally the connection between the extension and the barrel is biased toward a side of the barrel. In some embodiments, a needle cap 704 is mounted on extension 736. Optionally, the extension bends back and/or crosses the profile of the reservoir.

In some embodiments, a proximal portion of cartridge 700 may be designed with features that facilitate filling. For example, a flange 740 may be supplied on the proximal portion 702 of cartridge 700. For example, flange 740 may be used to hang barrel 742 from a syringe nest of an automatic filling machine. Optionally, a proximal surface (for example sealing surface 741 as illustrated in FIG. 7C) is configured for sealing to a vacuum device of a stoppering tube. In some embodiments, a distal opening 707 and/or a bore of a reservoir fits a standard plunger seal. For example, the bore may be cylindrical with smooth walls and/or a friction coefficient adjusted for proper plunger movement. Optionally, a proximal portion of barrel 742 (for example adjacent to flange 740) may be similar to a standard syringe (for example with a round outer cross section). Alternatively or additionally, a proximal section of the barrel may have a distinct shape and/or features (for example a squared shape and/or including a ridge and/or a groove). Alternatively or additionally, flange 740 may have a distinct shape and/or features. For example, the distinct shape and/or features may facilitate proper positioning and/or orienting of the cartridge in a syringe nest and/or in a drug delivery device.

In some embodiments, cartridge 700 may include asymmetric features. For example, the fluid path may be connected non-centrically to the distal end of barrel 742. For example, extension 736 projects from a distal end 709 of barrel 742. Optionally the connection between extension 736 and barrel 742 is biased to the dorsal side 739*a* of barrel 742. In some embodiments, a needle cap 704 is mounted on extension 736 at an approximately right angle to axis 758. For example, cap 704 faces towards the ventral side 739*b* of barrel 742. Optionally extension 736 and/or the mount for cap 704 is set back from a ventral side 739*b* of barrel 742. For example setting back extension 736 and/or the mount for cap 704 may facilitate designing a device with a lower profile (for example because the length of the mounting does not add to the profile of the device). Optionally, setting off the extension may help balance the cartridge. For example, balancing may facilitate vertical hanging of the cartridge. For example, balancing may facilitate handling of the cartridge, for example, spinning the cartridge to test for particles.

For example, the end of the extension may be set back between 0 and 1 mm from an edge of the barrel and/or between 1 and 3 mm and/or between 3 and 10 mm and/or more than 10 mm from the edge of the barrel. Alternatively or additionally, the extension may protrude beyond an opposite edge of the barrel.

For example, the end of the extension may protrude laterally between 0 and 1 mm beyond an edge of the barrel and/or between 1 and 3 mm and/or between 3 and 10 mm and/or more than 10 mm beyond the edge of the reservoir and/or barrel. In some embodiments, a cap mount may have a width (for example a diameter) ranging for example between 0 to 5 mm and/or between 5 to 10 mm and/or between 10 to 20 mm. In some embodiments, a width (for example a diameter) of a drug reservoir may range between 5 to 20 mm and/or between 10 to 14 mm and/or between 14 to 20 mm.

In some embodiments, cartridge 700 may include a fitting. Optionally a snap and/or a tab may be molded into a cartridge. For example, a fitting may include a plastic snap, a rivet, a pin, a cut out, an indentation, a protuberance, a snap clamp, a catch, a ball fitting, a latch, a barb etc. For example, a tab 738 and/or an indentation and/or a protuberance (for example tab 738, and/or protuberance 744 and/or 746) may be included in a cartridge. For example, a fitting may facilitate attachment of cartridge 700 to a drug delivery device (for example an auto-injector). In some embodiments, the fitting and/or a connection thereto may determine an orientation and/or inhibit rotation, for example with respect to the syringe nest and/or with respect to a drug delivery device.

In some embodiments, an indentation and/or a protuberance may be used to position cartridge 700 in a delivery device. For example tab 738 and/or protuberance 744, 746 may interact with an interlocking part of an injection device, for example a protuberance and/or indentation and/or catch and/or hole in the delivery device, to position the cartridge in the delivery device. For example, tab 738 may facilitate positioning the distal end 709 of cartridge 700 into alignment with the delivery device. For example as illustrated in FIG. 7B tab 738 may fit into a slot 731. Optionally a fitting may include a snap connector. For example, an indentation and/or protuberance could interlock to a pin and/or a matching hole. A bevel and and/or cutout and/or tab 748 may optionally interact with a complementary part in a delivery device (for example clips and/or snaps and/or a hole in the delivery device for example, as illustrated in FIG. 7B). Optionally tab 738 is within the profile of the barrel 742 of the cartridge (e.g. does not protrude laterally beyond the edge of barrel 742). For example, tab 738 does not interfere with inserting and/or removing the cartridge from a cartridge nest.

In some embodiments a fluid path connecting between cavity 732 of barrel 742 and extension 736 may pass through and/or be molded integrally to a cartridge 700. For example, the fluid path may pass through a molded extension of the reservoir. Optionally (for example as illustrated in FIG. 17B), a metal tube (for example needle 752) forms a portion of a fluid path. Optionally, dead space in the fluid path is reduced. For example, dead space may be reduced by including most and/or the entire fluid path inside needle 752, thus avoiding dead space in the plastic mold. For example, an embedded portion of needle 752 forms a bent fluid path to a protruding portion 751. Protruding portion 751 optionally protrudes straight out of extension 736. For example, protruding portion 751 protrudes substantially a right angle to axis 758 of the cavity 732 and/or the axis of barrel 742. A protruding end of needle 752 is optionally beveled and/or sharpened to facilitate insertion through the skin of a subject.

In some embodiments, a beveled needle tip 754 is oriented to avoid obstruction of needle 752. For example, the opening of beveled needle tip 754 is directed distally. In the case where needle tip 754 is inserted into a subject by pivoting around the proximal end of the cartridge and/or tends and/or when needle tip 754 tends to plow proximally as it is inserted into the subject, facing the opening of needle tip 754 distally may prevent needle obstruction.

In some embodiments, an extension may have a non-uniform cross section. For example, extension 736 has in I-beam cross section. For example in the center (web) section of extension 736 windows or channels 737 are formed. Optionally holding channels 737 are formed around needle supports that hold the needle during the molding process. Optionally, the needle supports are subsequently removed, leaving behind the empty channels 737. Optionally ribs 735 are offset from the fluid pathway. For example, the offset is sufficient to leave space for channels 737 around the fluid path and/or between ribs 735. Channels 737 are optionally formed in the molded part of a cartridge. For example, channels 737 may allow the needle to be held during the insert molding process. Optionally ribs 735 are within the profile of the barrel 742 of the cartridge (e.g. do not protrude laterally beyond the edge of barrel 742). For example, ribs 735 do not interfere with inserting and/or removing the cartridge from a cartridge nest.

In some embodiments, the end of extension 736 includes a mount for needle cap 704. For example, the mount may include a sealing ring 760 and/or a tapered section 761. For example, sealing ring 760 may seal against the inside of cap 704. In some embodiments, this may isolate the distal end of the extension optionally including a protruding section 751 of needle 752. For example, the cap may protect the distal end of extension 736 and/or protruding section 751 of needle 752 from contamination.

In some embodiments, a cap mount may include a tapered portion that physically holds the cap. For example, tapered portion 761 may be formed in ribs 735. In some embodiments, tapered section 761 may hold cap 704 rigidly to extension 736. Cap 704 may optionally be connected and/or disconnected from extension 736 by pulling and/or pushing cap 704 along the axis of extension 736 and/or along the axis of protruding section 751 of needle 752.

In some embodiments, a cartridge may be designed to reduce dead space. For example, a plunger may be user to drive fluid out from the reservoir. For example, the plunger may drive fluid towards a distal wall of the reservoir. Optionally fluid may pass through an opening in the distal wall to the fluid path of the extension. Optionally the plunger may be designed to initially contact the distal wall first far from opening. For example, as the plunger moves distally after first contacting the wall an increasing surface of the wall may contact the plunger. For example as the contact surface increases fluid may be driven along the distal wall towards the opening.

For example, at the end of travel of the plunger towards the distal wall of the cylinder under a force of ranging between 0-5 N and/or between 10-15 N and/or between 15-25 N the dead space between the plunger and the distal wall of the cylinder may range between 0.01 to 0.05 and/or 0.05 to 0.1 and/or between 0.1 to 0.5 ml. Optionally, the volume of the fluid path between the reservoir and the exit opening of the fluid path in a distal section of the extension may be small. For example, the internal volume of the fluid path from the reservoir to the opening of the extension may range between 0 to 0.01 and/or 0.01 to 0.03 and/or 0.03 to 0.06 and/or 0.06 to 0.1 and/or 0.1 to 0.5 ml.

FIG. 7C illustrates a proximal perspective view of a cartridge in accordance with an embodiment of the current invention. For example, a contact surface may be provided sized and/or shaped to facilitate connection to a filling machine. For example, a contact surface may include an annular surface 741. Optionally the annular surface 741 may have a width of 1 mm-20 mm For example surface 741 may facilitate connection to a vacuum device, for example for inserting a plunger seal into the reservoir. Alternatively or additionally, a size and shape of the cartridge may be fit for an automatic filling machine.

For example, the proximal portion of the cartridge may include gripping fittings such as a surface sized and shaped for an automated syringe holder and/or a flange 740. In some embodiments, the size of a flange and or contact surface may be non-uniform. Alternatively or additionally, a flange or gripping surface may have a uniform size and/or shape. The maximum width of the flange may range for example 5-20 mm. The minimum width of the flange may range for example 5-20 mm. optionally; the width of the flange may be greater for a larger cartridge and smaller for a smaller cartridge. For example, the thickness of the flange may range 1-3 mm.

In some embodiments, a mount for a needle and/or a cap may include for example a tapered luer and/or a slip luer and/or a luer lock.

Exemplary of a Syringe Nest with Cartridges

Figure 8A:
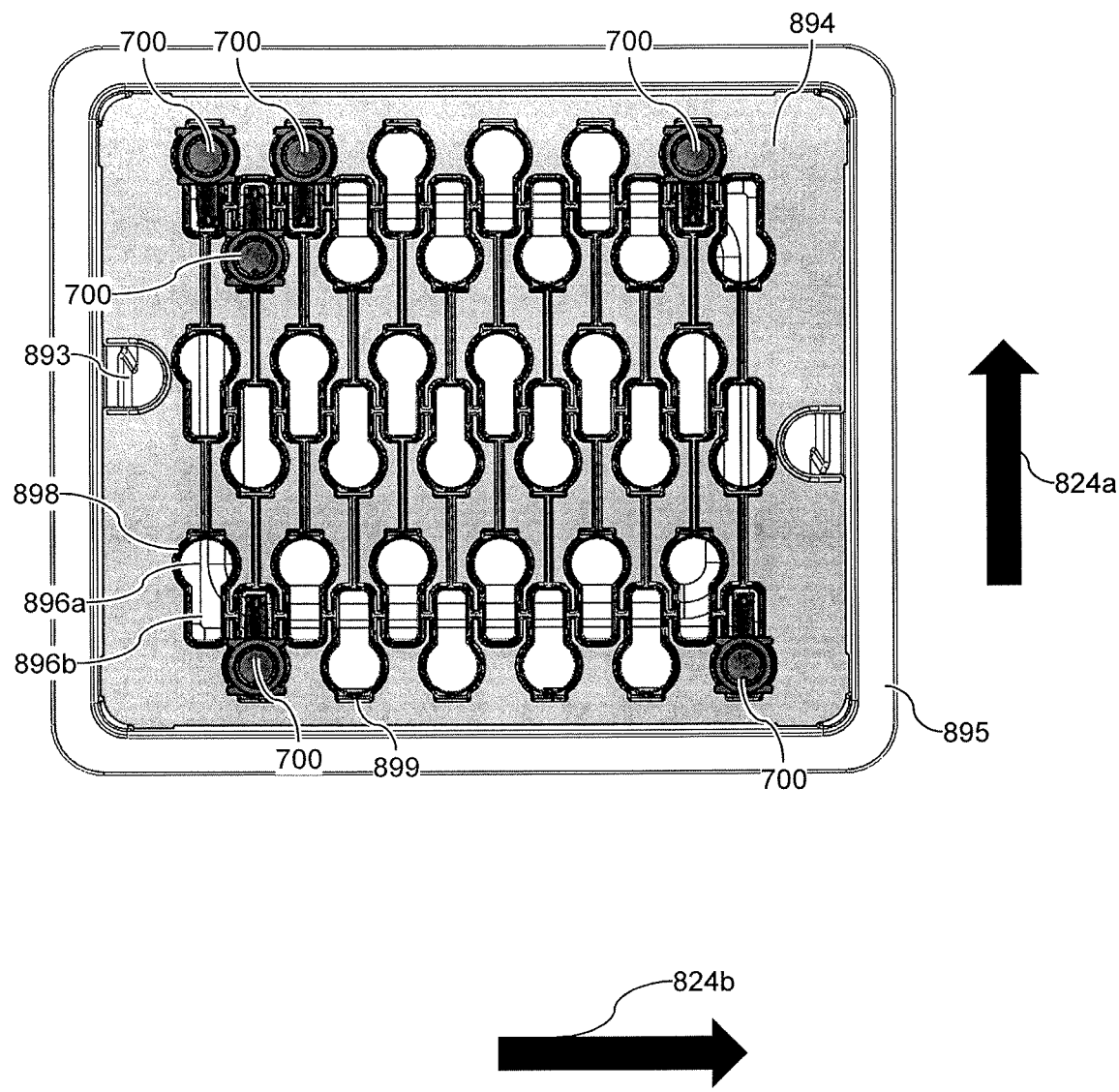

FIG. 8A is a top view of a syringe nest supporting an irregularly shaped cartridge in accordance with an embodiment of the current invention. For example, a syringe nest 894 includes collars that support one or more angled hub cartridges 700. Optionally, syringe nest 894 includes one or more spaced-apart openings. Optionally, the openings are arranged to save space and/or fit more cartridges in the syringe nest.

For example, in FIG. 8A, the nest is illustrated partially loaded with cartridges. Optionally, a nest may be supplied with each apertures loaded with a cartridges and/or empty of cartridges.

For example, the openings may be staggered and/or the orientation of the openings may alternate. In some embodiments, each opening may include a main aperture 896a and/or one or more extension apertures 896b. An opening is optionally shaped and/or sized to allow a first portion of cartridge 700 to pass through the opening. The syringe nest is optionally shaped and/or sized to support a second portion of a cartridge. For example, the openings may allow a distal portion of cartridge 700 to pass through while the syringe nest supports a proximal portion of the cartridge (for example a proximal flange 740). The syringe nest is optionally sized and/or shaped to fit an automated syringe filling machine and/or to orient one or more irregular cartridges 700 for filling by the automated syringe filling machine. For example, the syringe nest and/or cartridges 700 may fit a standard automated syringe-filling machine.

In some embodiments, the syringe nest may include a collar 898. Optionally, collar 898 extends upward from the face of syringe nest 894. For example, collar 898 supports cartridge 700. Alternatively or additionally, a collar may extend downwards from and/or at an arbitrary angle to the face of the syringe nest. Optionally a collar may completely and/or partially surround an opening (for example main aperture 896a and/or extension aperture 896b). Optionally a collar may have a uniform and/or non-uniform height and/or thickness.

In some embodiments, openings and/or collars 898 are arranged in a series of staggered rows and/or columns. Additionally or alternatively, openings and/or collars 898 are arranged in a series of uniformly spaced rows and/or columns. Optionally, syringe nest 894 includes cutout handles 893 for example for lifting and/or easily gripping and/or orienting syringe nest 894 during various processing and/or filling operations.

In some embodiments, syringe nest 894 is positioned in a tub 895. Tub 895 optionally includes a stepped portion supporting syringe nest 894.

Optionally, syringe nest 894 may be filled in different directions. For example, syringe nest 894 is invariant to rotation around 180 degrees. syringe nest 894 may optionally be filled progressing in the direction of arrow 824a. For example, in that direction, the cartridges are filled as six columns of six cartridges each. Alternatively or additionally, syringe nest 894 may optionally be filled progressing in the direction of arrow 824b. For example, in that direction, the cartridges are filled as twelve columns of three cartridges each.

Figure 8B:
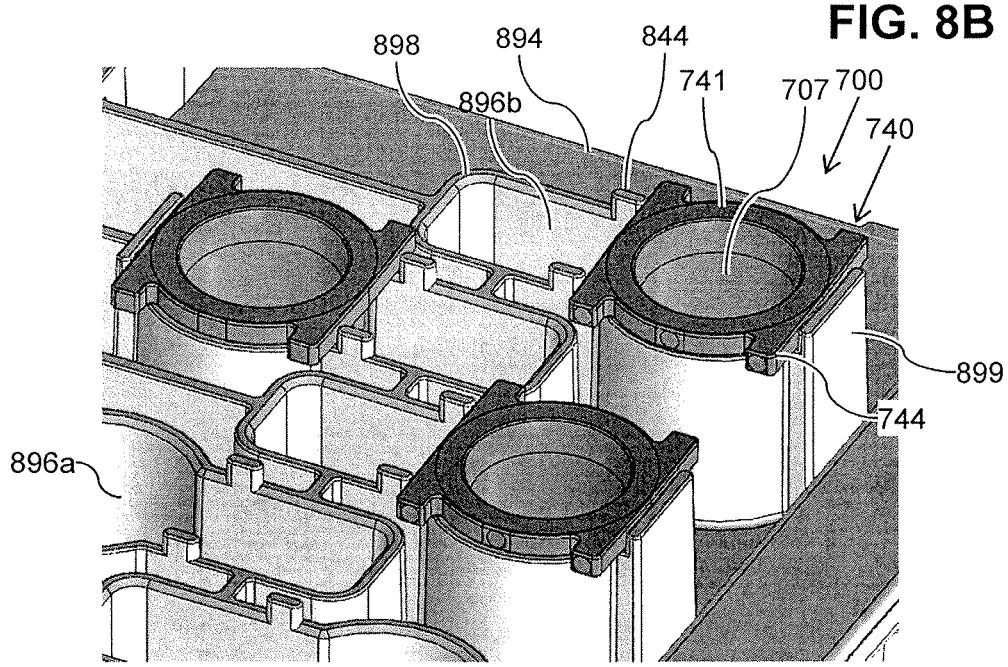

FIG. 8B is a perspective view of supporting an angled needle cartridge hanging from a syringe nest in accordance with an embodiment of the current invention. Optionally holes in syringe nest 894 are sized and shaped to fit a distal portion of an irregularly shaped cartridge. For example, a hole may allow a distal portion of cartridge 700 to pass therethrough.

In some embodiments, extension aperture 896b is less wide than main aperture 896a and/or radiates outward from main aperture 896a for example giving the hole a keyhole shape. For example aperture 896a may be sized and shaped to allow a cartridge barrel to fit therethrough (for example with a tolerance of less than 0.01 mm and/or ranging between 0.01 to 0.1 mm and/or between 0.1 to 0.5 mm and/or ranging between 0.5 to 2 mm and/or more than 2 mm). Optionally, extension aperture 896b is sized and shaped to allow a protruding portion of the cartridge to pass therethrough (for example with a tolerance of less than 0.01 mm and/or ranging between 0.01 to 0.1 mm and/or between 0.1 to 0.5 mm and/or ranging between 0.5 to 2 mm and/or more than 2 mm). For example, extension apertures 896b allow a protruding portion of needle 752 and/or a needle cap, for example needle cap 704 to pass through. Optionally, the complete aperture 896b and 896a is sized and shaped to allow a distal portion of the cartridge to pass therethrough (for example with a tolerance of less than 0.01 mm and/or ranging between 0.01 to 0.1 mm and/or between 0.1 to 0.5 mm and/or ranging between 0.5 to 2 mm and/or more than 2 mm).

In some embodiments, a collar and/or a hole may be shaped to orient the cartridge and/or reservoir. For example a rear protrusion 899 on some or all of the holes of syringe nest 894 orients cartridge 700 around the axis of its internal cylindrical space and/or orients a protruding portion of the cartridge (for example needle cap 704). For example a front protrusion 844 on some or all of the holes of syringe nest 894 orients cartridge 700 around the axis of its internal cylindrical space and/or orients a protruding portion of the cartridge (for example needle cap 704). For example, a protrusion 899 and/or 844 may interlock with an orientation feature (for example a flat surface) on the flange of a cartridge 700. Optionally, alternating caps 704 are oriented in the opposite directions. Alternatively or additionally, cartridges may be oriented in the same and/or varying directions.

In some embodiments, a cartridge mount and/or an orientation feature may include lead in bevel and/or chamfer 891 (for example, as illustrated in FIG. 8C). For example, the chamfer may facilitate orientation of the cartridge. For example, the chamfer may prevent the cartridge from getting hung up during IPC replacement. Alternatively or additionally, a portion of the cartridge (for example the barrel and/or the flange) may be tapered.

In some embodiments, a collar and/or the sides of an opening in a syringe nest may support a proximal portion of a syringe and/or cartridge. For example, collar 898 and/or the sides of holes in syringe nest 894 may support and/or orient barrel 742 (for example, the proximal portion thereof for example a proximal flange 740 thereof). Alternatively or additionally, a syringe nest may have other protrusions, holes and/or indentations for supporting and/or stabilizing the cartridge. For example, a syringe nest may have a pin that passes through a hole in a proximal flange of the cartridge and/or a hole through which passes a pin on a proximal flange of the cartridge.

An opening, hole, indentation, protrusion and/or a pin may be tapered and/or beveled. The dimensions of the syringe nest are optionally configured so that the ends of the cartridge barrels are spaced from bottom wall of tub 895. In other embodiments, the distal ends of cartridges may contact the bottom wall of tub 895. Alternatively or additionally, a syringe nest may have a hanger on its bottom side and/or a single cartridge may be connected to the syringe nest at more than one location. Alternatively or additionally, other geometries are possible within the spirit of the invention. For example, a cartridge may have a needle connected to a flexible tube.

Optionally the tube and needle may be strapped to the side of the cartridge and fit into a orifice and extension and/or the needle and/or tube may string back through the extension and sit on top of the syringe nest and/or the needle and tube may string back through the extension and hang through a second hole in the syringe nest and/or the needle and tube may string back hang from a hook on the bottom of the syringe nest and/or the needle and tube may sit on the bottom of the tub etc.

In some embodiments, tub 895 may be closed and/or sealed in a cover bag and/or wrapper, for example before or after filling the cartridges. In some embodiments, protective layer of sheet material, such as polyethylene, foam or other plastic, may be positioned to cover syringe nest 894 and/or cartridges. Optionally, the sheet is substantially the same size and/or slightly larger than syringe nest 894. A closure or cover sheet optionally seals over tub 895 to completely enclose the array of cartridge barrels. For example, the cover sheet may include a thermoplastic material that is heat-sealed to a flange on tub 895 to form a complete seal. For example a cover sheet may be made of a gas-permeable material such as a spun bonded polyolefin sold under the trademark TYVEK by E.I. DuPont & Co. In some embodiments, the covering allows the cartridges to be gas sterilized, if desired, while they are in the sealed tub 895. In further embodiments, the cartridge barrels can be sterilized by radiation and/or another means.

FIG. 8C illustrates a clearance for a contact surface in accordance with an embodiment of the current invention. In some embodiments, a contact surface of a cartridge may clear a portion of a syringe nest. For example, contact surface 741 may clear a protrusion (e.g. protrusion 899 and/or 844) of a syringe nest by extending beyond the protrusion by a clearance 892. Optionally the clearance 892 facilitates access to the proximal end of the cartridge, for example by a vacuum stopper inserter. For example, clearance 892 may equal the difference between the thickness of flange 740 and the height of protrusion 844 and/or 899. Optionally, clearance 892 may range between 0.5-2 mm. For example, the thickness of flange 740 may range between 1-3 mm. For example, the height of protrusion 844 and/or 899 may range between 0.5-2 mm. In some embodiments clearance 892 may inhibit puncture of a covering of the nest. For example, when a full nest is covered by a vacuum bag, clearance 892 may inhibit puncturing of the bag by protrusions 844.

FIG. 8D illustrates a cartridge hanging from a syringe nest in accordance with an embodiment of the current invention. For example, syringe nest may be sealed in a tub 895 with a top cover 811. For example, a top cover may be made of Tyvek® available from DuPont™, E. I. du Pont de Nemours and Company 1007 Market Street Wilmington, Del. 19898.

Examples of Alternative Syringe Nests

FIG. 9A-9C are a schematic diagrams of alternative cartridge syringe nests in accordance with embodiments of the present invention.

FIGS. 9A-9B illustrate a syringe nest 994*a* including 36 cartridge mounts and/or apertures 996 in accordance with an embodiment of the current invention. syringe nest 994*a* is not invariant over 180-degree rotation either in the small direction 924*b* or in the large direction 924*a*. Optionally some filling machines may fill a syringe nest, which is fed always in the same orientation. Optionally, a position control mechanism may be supplied with a printed sign on a tub and/or syringe nest and/or a top cover. Optionally the sign may be read out by the filling machine. A cartridge packer may optionally orient the nest so that the sign is visible. The filling machine may include a sensor detecting the correct nest orientation and/or an actuator to turn the tub or the nest or to refuse filling.

Optionally, the row to row and/or column to column distance is equal for all rows and/or columns of syringe nest 994*a*. Optionally, the distance is large enough to allow filler tube and/or stopper placement unit movement. Optionally, columns do not overlap in syringe nest 994*a*. For example, the lack of overlap may facilitate lifting cartridges column by column, for example, to allow access of the IPC grippers to the container.

FIG. 9C illustrates a syringe nest 994*b* including 48 cartridge mounts and/or apertures 996 in accordance with an embodiment of the current invention. The nest is optionally rotation invariant over 180 degree rotation.

In some embodiments, progressing in direction 924*d*, syringe nest 994*b* includes eight columns of six cartridge mounts per column. The column to column distance along syringe nest 994*b* progressing in the direction 924*d* may optionally not be equal. A filling machine for this configuration would optionally have variable filling tubes needles and the piston placement. The distance is optionally configured to allow needle and stopper placement unit movement (for example the distance may be within a range specified for a specific filling machine and/or all of the distances may be equal etc.). Optionally, in this configuration, the columns of cartridges overlap. For example, the intervening columns may interfere when lifting a column from below with a lifting bar. Optionally, a lifting bar may have protrusions and/or indentations on upper surface to lift the desired cartridges without disturbing intervening cartridges.

In some embodiments, progressing in direction 924*c*, syringe nest 994*b* includes twelve columns of four columns per column. Row to row distance is optionally equal for all rows and columns. The columns do not overlap, facilitating lifting of containers column by column, for example to allow access of the IPC grippers.

Figure 10:
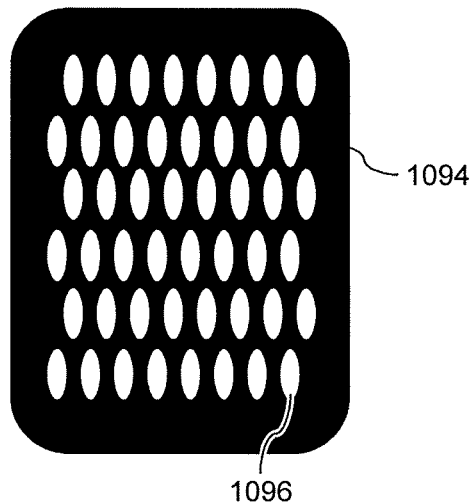
FIG. 10 is a schematic diagram of an alternative syringe nest in accordance with an embodiment of the present invention.

FIG. 10 is a schematic diagram of an alternative syringe nest in accordance with an embodiment of the present invention. For example, a syringe nest 1094 may include oval apertures 1096 and/or other regular and/or irregular shaped apertures.

Figure 11A:
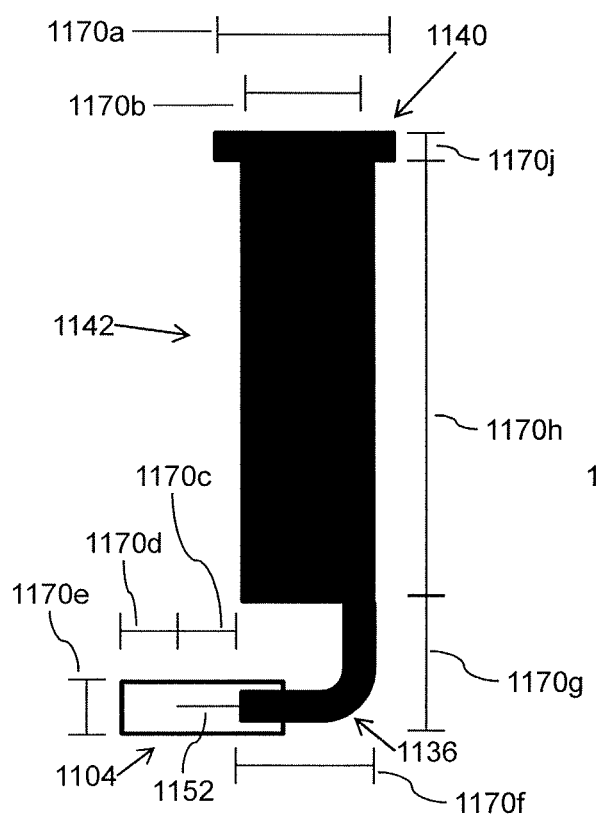
FIGS. 11A and 11B are schematic diagrams of a cartridge in accordance with an embodiment of the present invention.
Figure 11B:
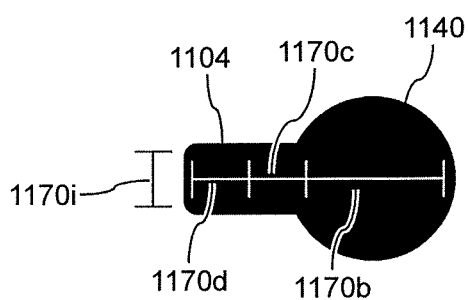
Figure 12A:
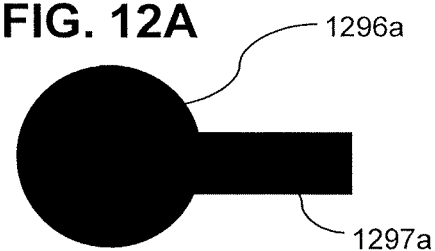
FIG. 12A-12E are schematic views of various exemplary geometries for openings in a syringe syringe nest in accordance with an embodiment of the current invention.
Figure 12E:
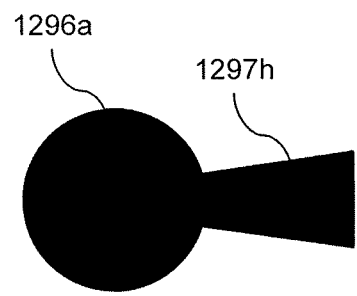
Figure 12B:
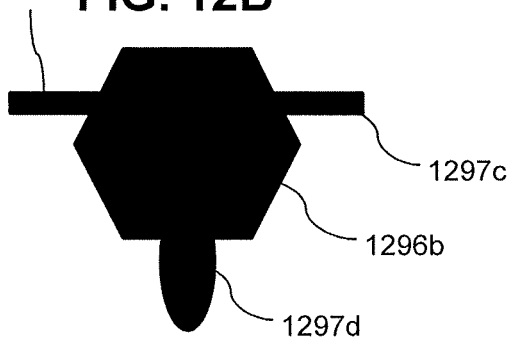
Figure 12C:
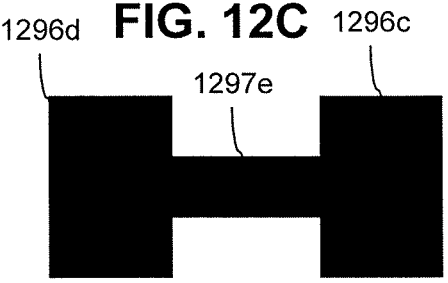
Figure 12D:
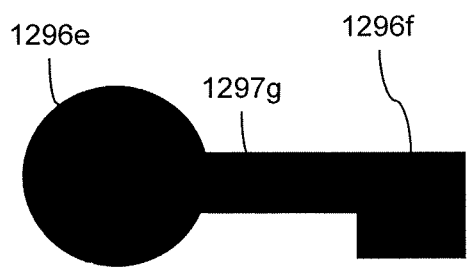

FIGS. 11A and 11B are schematic diagrams of a cartridge in accordance with an embodiment of the present invention.

In some embodiments a cartridge may include a reservoir 1142. A distal portion of reservoir 1142 may include a lateral protrusion. For example, the lateral protrusion may include an extension 1136. For example, the protrusion may include a needle 1152 and/or a needle cap 1104.

In some embodiments, reservoir 1142 may include a barrel section. Optionally, the proximal portion of the barrel where it contacts a flange 1140 may have a cross sectional width 1170*b* ranging between 1 to 6 mm and/or between 6 to 12 mm and/or between 12 to 24 mm and/or between 24 to 48 mm. For example, the barrel may be cylindrical and/or have a circular cross section. Optionally, the barrel may have a length 1170*h* ranging between 1 to 6 mm and/or between 6 to 12 mm and/or between 12 to 25 mm and/or between 25 to 50 mm and/or between 50 to 100 mm and/or between 50 to 100 mm and/or between 100 to 200 mm. Alternatively or additionally, the cross section of the barrel may change over its length and/or be non-circular.

In some embodiments, a flange 1140 may have a width 1170*a* that is between 0 to 2 mm and/or 2 to 6 mm and/or 6 to 12 mm and/or 12 to 25 mm greater than the proximal portion of the barrel. Optionally a thickness 1170*j* of between 0 to 0.5 mm and/or between 0.5 to 1 mm and/or between 1 to 2 mm and/or between 2 to 4 mm and/or between 4 to 8 mm and/or between 8 to 16 mm.

In some embodiments a cartridge may include a distal extension 1136. For example the extension may extend distally from the barrel a length 1170*g* ranging between 0 to 2 mm and/or 2 to 5 mm and/or 5 to 10 mm and/or 10 to 20 mm and/or 20 to 40 mm. The extension optionally includes a curved section and/or extends laterally. For example, the extension may include a molded section that extends laterally a distance 1170*f* ranging between 0 to 2 mm and/or 2 to 5 mm and/or 5 to 10 mm and/or 10 to 20 mm and/or 20 to 40 mm. Optionally, the lateral extension of the molded portion is within the profile of the barrel. Alternatively or additionally, the molded portion may extend beyond the edge of the barrel for example, for a distance ranging 0 to 2 mm and/or 2 to 5 mm and/or 5 to 10 mm and/or 10 to 20 mm and/or 20 to 40 mm.

In some embodiments a lateral extension includes a needle 1152. For example, the needle may extend straight from the molded portion of extension 1136. For example the needle may include an external portion that extends laterally out of the reservoir and/or out of the molded part of the extension for example for a distance 1170*c* ranging between 1 and 3 mm or 3 and 7 mm or 7 and 8 or 8 and 10 mm or 10 and 15 mm or 15 and 50 mm. A needle cap 1104 may cover the needle. The needle cap optionally extends laterally beyond the needle. For example the length 1170*d* of the needle cap extending laterally beyond the end of the needle may range between 0 to 2 mm and/or 2 to 5 mm and/or 5 to 10 mm and/or 10 to 20 mm and/or 20 to 40 mm. The cover optionally has a width 1170*e* in a longitudinal direction and a width 1170*i* in the lateral direction. Optionally widths 1170*e* and 1170*i* are approximately equal (for example, cap 1104 may have a circular cross section).

FIG. 12 illustrates some alternative shapes of openings in a cartridge syringe nest in accordance with some embodiments of the current invention. In some embodiments, the openings may have various geometries. For example an opening may be key hole shaped (for example with one orifice 1296*a* and one extension 1297*a* as illustrated in FIG. 12A). Optionally, an extension 1297*h* may be trapezoidal as illustrated for example in FIG. 12E. For example, trapezoidal extension 1297*h* may make it possible to insert and/or remove an irregular cartridge even when it has become slightly mis-oriented. An irregular shaped opening may optionally have one orifice 1296*b* and/or multiple extensions 1297*b*, 1297*c*, 1297*d* (for example as illustrated in FIG. 12B). For example, the shape of FIG. 12B may be useful for a reservoir for a drug delivery device that has protrusions and/or flanges to secure the reservoir to the device. Additionally or alternatively an opening may have multiple orifices and a single extension for example barbell shaped (for example a symmetric barbell as illustrated in FIG. 12C with orifices 1296*c* and 1296*d* and extension 1297*e* and/or an asymmetric barbell as illustrated in FIG. 12D with orifices 1296*e* and 1296*f* and extension 1297*g*).

For example, a barbell shaped opening might be useful to fill multipart reservoirs. For example a reservoir may consist of a cartridge barrel connected by a flexible tube to a needle having a flange and needle cover. The barrel could be supported, for example, in orifice 1296*e* while the tube passes under the syringe nest through extension 1297*g* and the needle assembly is supported on orifice 1296*f*. Orifices and/or extensions of the openings may optionally be curved and/or angled. Orifices and/or extensions of the openings may be for example circular, oval, hexagonal, trapezoidal, pentagonal, rectangular etc. Orifices and/or extensions of the openings may optionally be regularly and/or irregularly shaped. Orifices and/or extensions of the openings may optionally be symmetric across one or more axes and/or asymmetric. A single syringe nest may optionally include multiple openings having a similar geometry and/or openings of different geometries. Separate openings may be optionally connected and/or disconnected from each other. Multiple openings on a single syringe nest may optionally be oriented in the same direction and/or in different directions. For example, openings may be arranged in a 2D and horizontal array.

Figure 13:
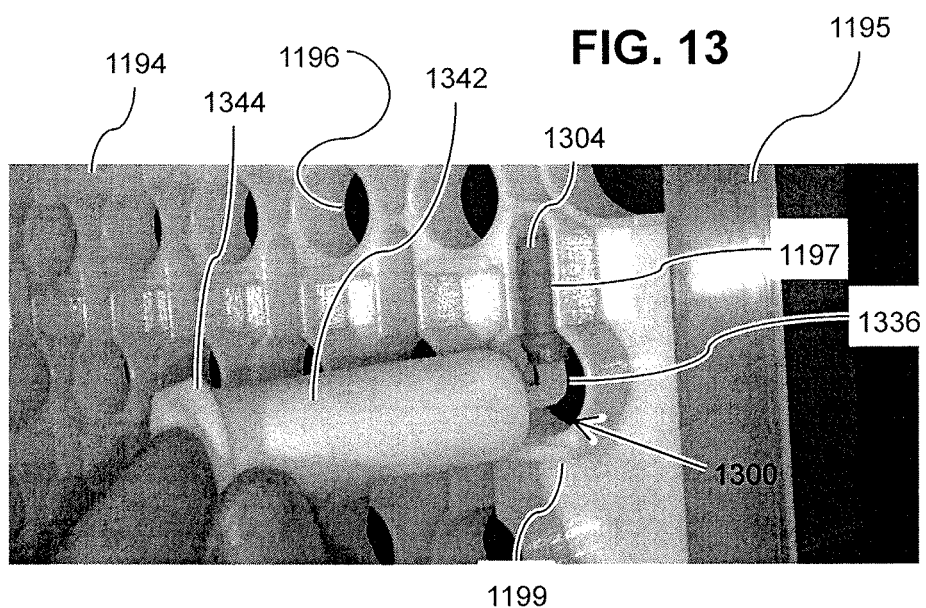
FIG. 13 is a photograph of inserting an angled needle cartridge into a syringe nest in accordance with an embodiment of the current invention.

FIG. 13 is a photograph of inserting an angled needle cartridge through a hole into a syringe nest in accordance with an embodiment of the current invention. Optionally holes in syringe nest 1194 are sized and shaped to fit a distal portion of an irregularly shaped cartridge and/or allow the distal portion to fit through the hole. For example a hole may allow a distal portion of cartridge 1300 and/or a cartridge as illustrated in FIGS. 4A-5B to pass therethrough.

In some embodiments, extension 1197 is thinner than orifice 1196 and/or radiates outward from orifice 1196 giving the hole a keyhole shape. For example orifice 1196 may be sized and shaped to allow a distal portion of a cartridge barrel to fit through the opening (for example with a tolerance of less than 0.01 mm and/or ranging between 0.01 to 0.1 mm and/or between 0.1 to 0.5 mm and/or ranging between 0.5 to 2 mm and/or more than 2 mm). For example orifice 1196 fits barrel 742 and/or 1342. Optionally, extension 1197 is sized and shaped to allow a protruding portion of the cartridge to pass through (for example with a tolerance of less than 0.01 mm and/or ranging between 0.01 to 0.1 mm and/or between 0.1 to 0.5 mm and/or ranging between 0.5 to 2 mm and/or more than 2 mm). For example, extension 1197 fits the protruding portion of the cartridge. For example, extensions 1197 allow a protruding portion 751 of needle 752 and/or a needle cap for example needle cap 704 and/or needle cap 1304 to pass through.

Figure 14:
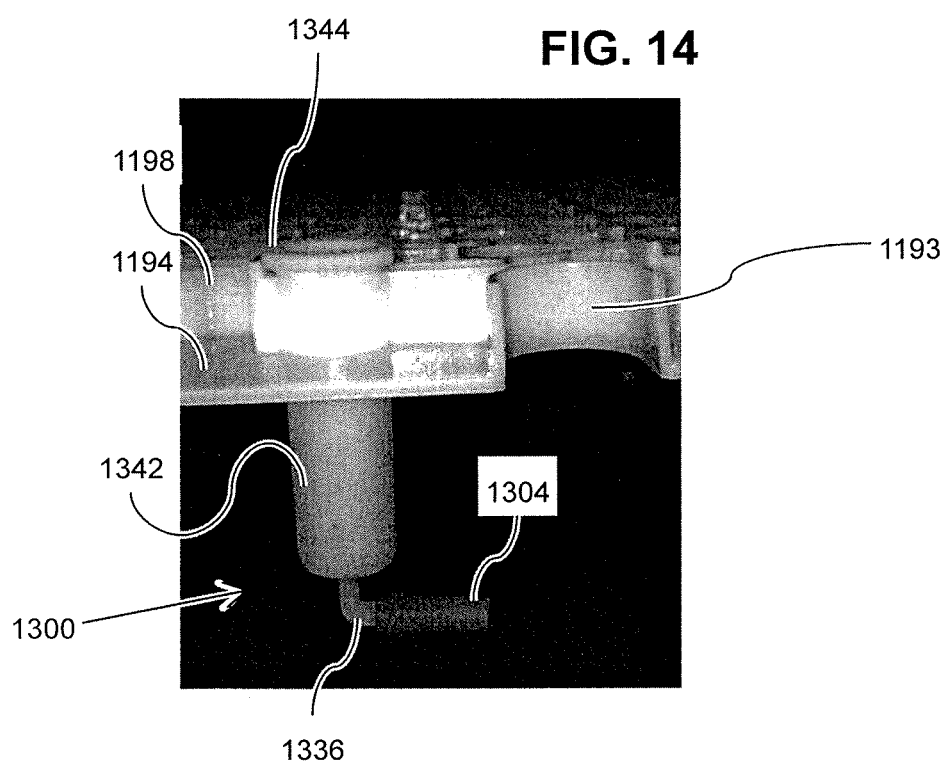
FIG. 14 is a photograph of supporting an angled needle cartridge on a syringe nest in accordance with an embodiment of the current invention.

FIG. 14 is a photograph of supporting an angled needle cartridge hanging from a syringe nest in accordance with an embodiment of the current invention.

In some embodiments, a collar and/or a hole may be shaped to orient the cartridge and/or reservoir. For example a rear protrusion 1199 on each hole of syringe nest 1194 orients barrel 1342 around the axis of its internal cylindrical space and/or orients a protruding portion of the cartridge (for example a hub 1336 and/or needle cap 1304). For example syringe nest 1194 orients all hubs 1336 and/or caps 1304 in the same direction. Optionally a collar and/or the sides of an opening in a syringe nest may support a proximal portion of a syringe and/or cartridge. For example, collar 1198 and/or the sides of holes in syringe nest 1194 may support and/or orient barrel 742 and/or 1342 (for example the proximal portion, for example a proximal flange 744 and/or 1344). Alternatively or additionally, a syringe nest may have other protrusions, holes and/or indentations for supporting and/or stabilizing the cartridge. For example, a syringe nest may have a pin that passes through a hole in a proximal flange of the cartridge and/or a hole through which passes a pin on a proximal flange of the cartridge. An opening, hole, indentation, protrusion and/or a pin may be tapered and/or beveled for example with an insertion chamfer. The dimensions of the syringe nest and/or may be configured so that an end of a cartridge barrel is spaced from bottom wall of tub 1195. In other embodiments, an end of a cartridge barrel may contact the bottom wall of tub 1195. Alternatively or additionally a syringe nest may have a hanger on its bottom side and/or a single cartridge may be connected to the syringe nest at more than one location. Alternatively or additionally other geometries are possible within the spirit of the invention. For example, a cartridge may have a needle connected to a flexible tube. Optionally the tube and needle may be strapped to the side of the cartridge and fit into a orifice and extension and/or the needle and tube may string back through the extension and sit on top of the syringe nest and/or the needle and tube may string back through the extension and hang through a second hole in the syringe nest and/or the needle and tube may string back hang from a hook on the bottom of the syringe nest and/or the needle and tube may sit on the bottom of the tub etc. Syringe nest 1194 optionally includes a handle 1193.

In some embodiments, tub 1195 may be enclosed in a sealed bag and/or a wrapper, for example before or after filling the cartridges. In some embodiments, a protective layer of sheet material, such as polyethylene, foam or other plastic, may be positioned to cover syringe nest 1194 and/or the cartridge barrels. Optionally, the sheet is substantially the same size as syringe nest 1194. A closure or cover sheet optionally seals over tub 1195, for example, to completely enclose the array of cartridge barrels. For example, the cover sheet may include a thermoplastic material that is heat-sealed to a flange on tub 1195. For example a cover sheet may be made of a gas-permeable material such as a spun bonded polyolefin sold under the trademark TYVEK by E.I. DuPont & Co. In some embodiments, this allows the cartridge barrels to be gas sterilized, if desired, while they are in the sealed tub 1195. In further embodiments, the cartridge barrels can be sterilized by radiation and/or another means.

Figure 15:
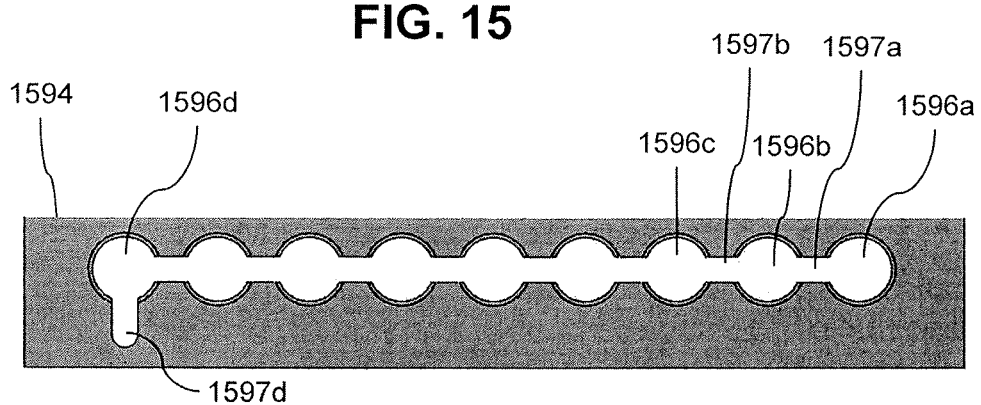
FIG. 15 is a schematic view of a syringe syringe nest wherein one or more cartridges are inserted to a linear series of openings and then reoriented in accordance with an embodiment of the present invention.
Figure 16:
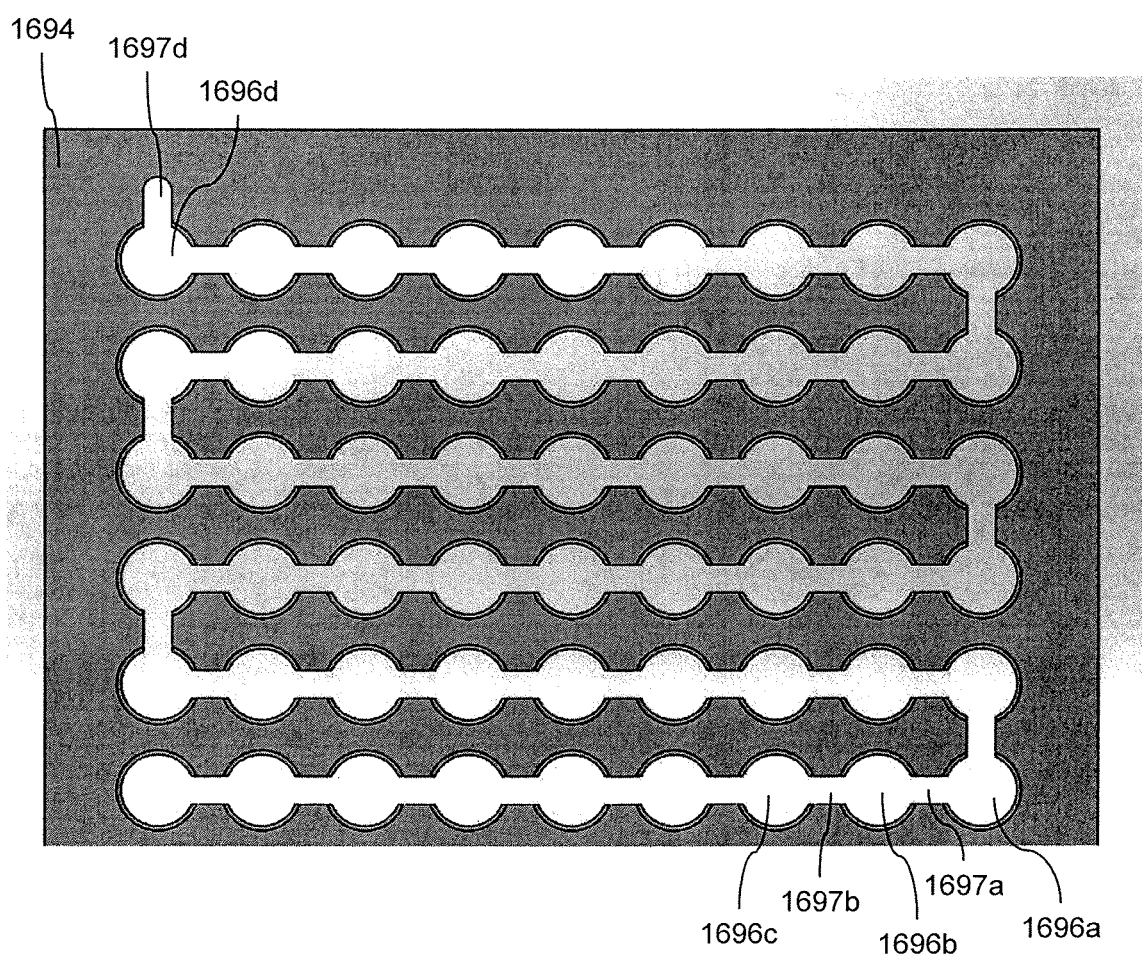
FIG. 16 is a schematic view of a syringe syringe nest wherein one or more cartridges are inserted to a winding series of openings and then reoriented in accordance with an embodiment of the present invention.

FIGS. 15 and 16 are schematic views of a cartridge syringe nest wherein a cartridge is inserted and then reoriented in accordance with some embodiments of the present invention. In some embodiments, a filling machine may be modified for reorienting a cartridge in a syringe nest.

In some embodiments (for example as illustrated in FIG. 15), a syringe nest 1594 includes an extended opening including a series of interconnected orifices and extensions arranged in a line. An irregular cartridge (for example cartridge 1300) is optionally inserted through an orifice and extension and then reoriented to make space for a further cartridge. In some embodiments, parts of two different cartridges may be inserted through a single orifice and/or extension. Optionally reusing the same orifice and/or extension may save space and/or facilitate packing more cartridges into a syringe nest.

In some embodiments, a first cartridge (for example cartridge 1300) barrel is inserted through orifice 1596*a* while a protrusion of the cartridge (for example needle cap 1304) is directed towards the next orifice 1596*b* (for example leftward in FIG. 15) and/or passes through extension 1597*a*. Optionally, the protrusion is longer than extension 1597*a* and part of the protrusion passes through orifice 1596*b*. Once the protrusion has cleared the bottom surface of syringe nest 1594, the cartridge is optionally reoriented by rotation for example ranging between 20 to 30 degrees and/or 30 to 60 degrees and/or 60 to 90 degrees and/or between 90 to 160 degrees. Rotation of the cartridge optionally moves the protrusion away from orifice 1596*b* clearing orifice 1596*b*. Optionally after reorienting, the cartridge is further lowered and its orientation locked by a collar. In some embodiments, once orifice 1596*b* is clear, a second cartridge barrel is inserted through orifice 1596*b* with its protrusion passing through extension 1597*b* and/or orifice 1596*c*. Then the second cartridge is optionally reoriented clearing orifice 1596*c*. With orifice 1596*c* clear, a third cartridge barrel optionally fits through orifice 1596*c*. Optionally, cartridges are continuously inserted and reoriented until the ninth cartridge is inserted into orifice 1596*d* and/or extension 1597*d*. Once the cartridges are inserted and/or reoriented, the filling process optionally begins.

In some embodiments, removal of cartridges is the reverse of insertion. For example in the embodiment of FIG. 15, the ninth cartridge is removed from orifice 1596*d* and/or extension 1597*d* and then the eighth cartridge is reoriented serially down to the second cartridge which is removed from orifice 1596*b* and/or through orifice 1596*c* and/or extension 1597*b*. Once orifice 1596*b* is clear, the first cartridge is optionally removed, the barrel passing through orifice 1596*a* and/or through protrusion passing through orifice 1596*b* and/or extension 1597*a*.

In some embodiments (for example as illustrated in FIG. 16), a syringe nest 1694 includes an extended opening including a series of interconnected orifices and extensions that form a non-linear pattern. For example, the interconnected orifices and extensions may form a snake like pattern as illustrated for example in FIG. 16. An irregular cartridge (for example cartridge 1300) is optionally inserted through an orifice and extension and then reoriented to make space for a further cartridge.

In some embodiments, a first cartridge (for example cartridge 1300) barrel is inserted through orifice 1696*a* while a protrusion of the cartridge (for example needle cap 1304) is directed towards the next orifice 1696*b* (for example leftward in FIG. 15) and/or passes through extension 1697*a*. Optionally, the protrusion is longer than extension 1697*a* and part of the protrusion passes through orifice 1696*b*. Once the protrusion has cleared the bottom surface of syringe nest 1694, the cartridge is optionally reoriented by rotation for example ranging between 20 to 30 degrees and/or 30 to 60 degrees and/or 60 to 90 degrees and/or between 90 to 160 degrees. Rotation of the cartridge optionally moves the protrusion away from orifice 1696*b* clearing orifice 1696*b*. Optionally after reorienting the cartridge is further lowered and its orientation locked by a collar. In some embodiments, once orifice 1696*b* is clear, a second cartridge barrel is inserted through orifice 1696*b* with its protrusion passing through extension 1697*b* and/or orifice 1696*c*. Then the second cartridge is optionally reoriented clearing orifice 1696*c*. With orifice 1696*c* clear, a third cartridge barrel optionally fits through orifice 1696*c*. Optionally, cartridges are continuously inserted and reoriented along a twisting path until the fifty fourth cartridge is inserted into orifice 1696*d* and/or extension 1697*d*. The twisting pattern interconnected orifices and/or extensions of FIG. 16 may optionally increase the number of cartridges fit into a syringe nest over a static positioning of cartridges (where the orientation of insertion is also the orientation of filling) and/or a pattern of disconnected openings in a syringe nest. Optionally removing the cartridges is the inverse of insertion starting with the fifty fourth cartridge and going back to the first cartridge.

Figure 17A:
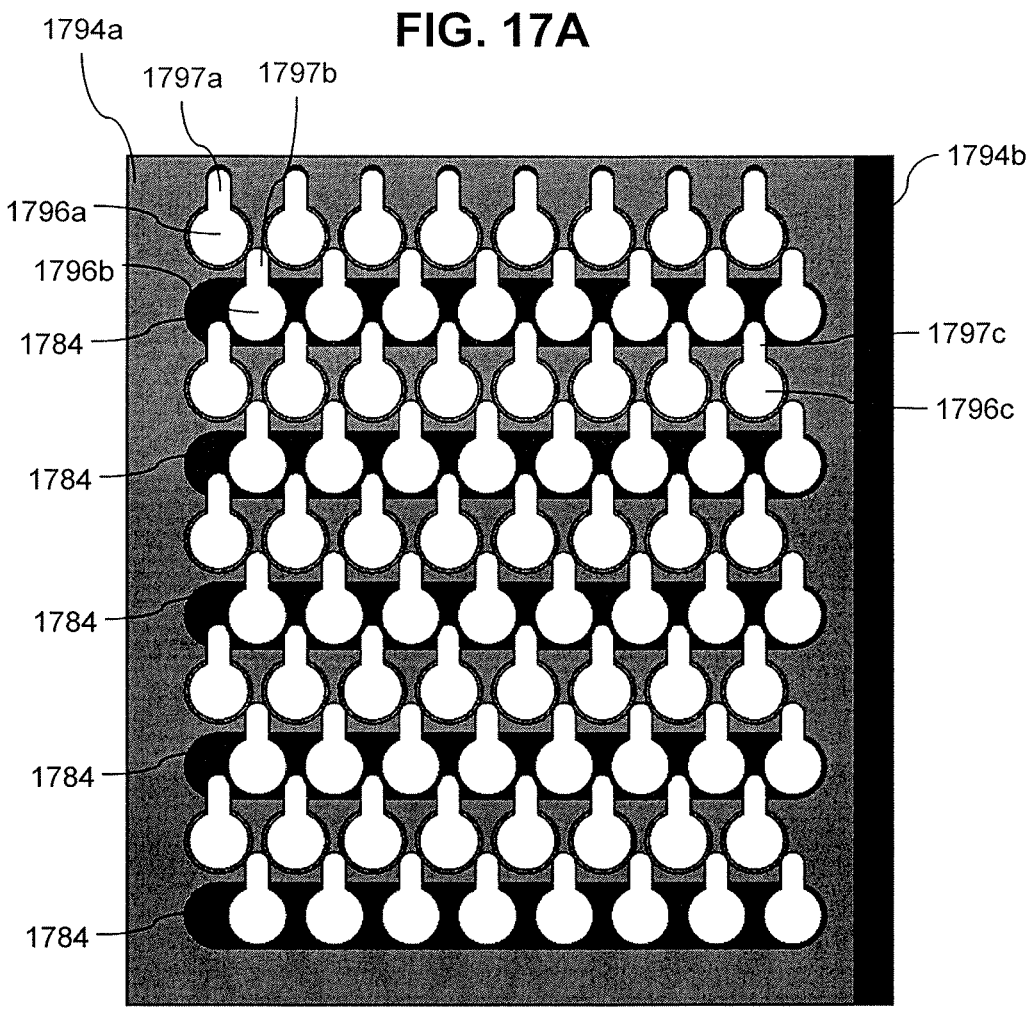
FIGS. 17A-17D illustrate an extending syringe syringe nest with irregular openings in accordance with an embodiment of the present invention.
Figure 17B:
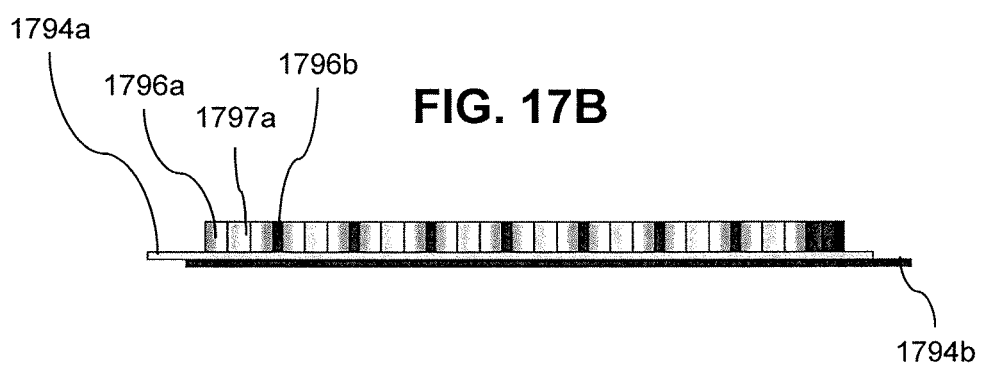
Figure 17C:
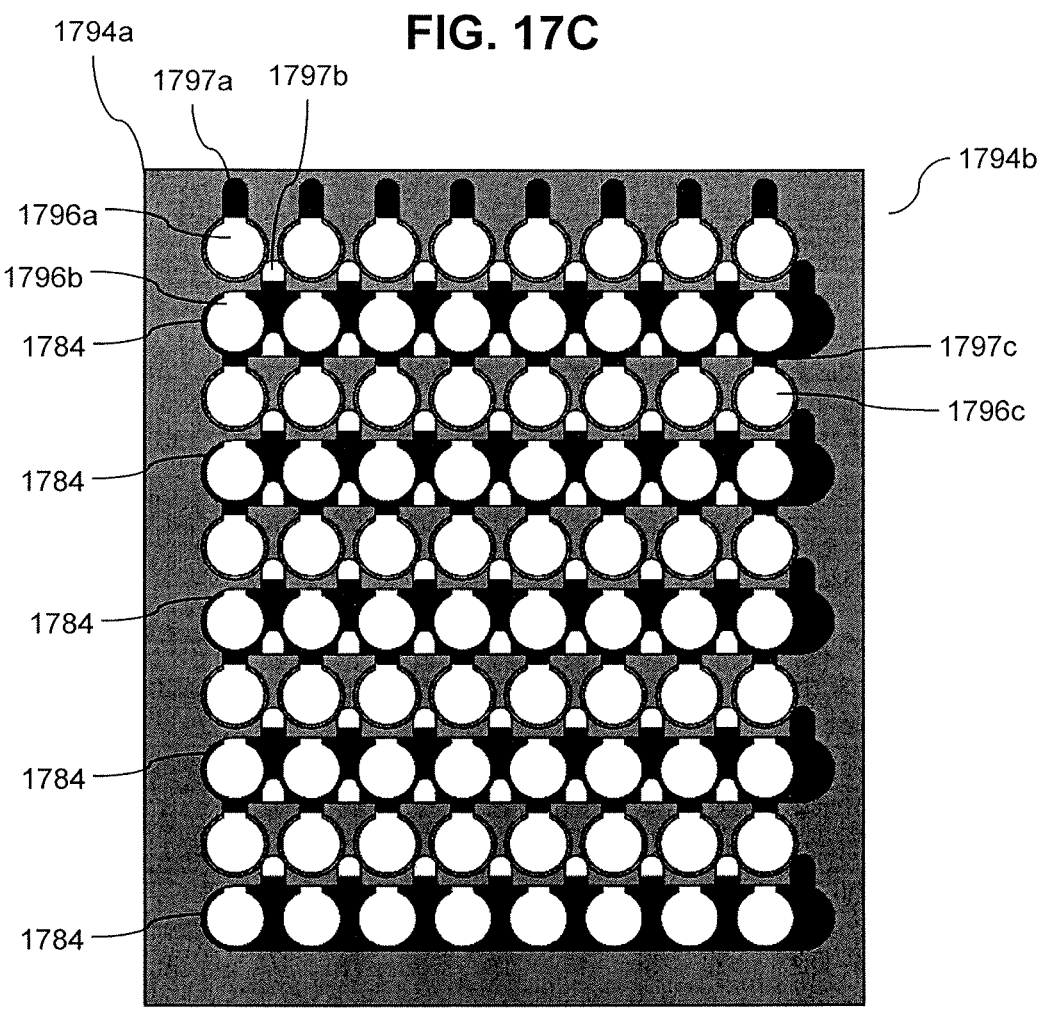
Figure 17D:
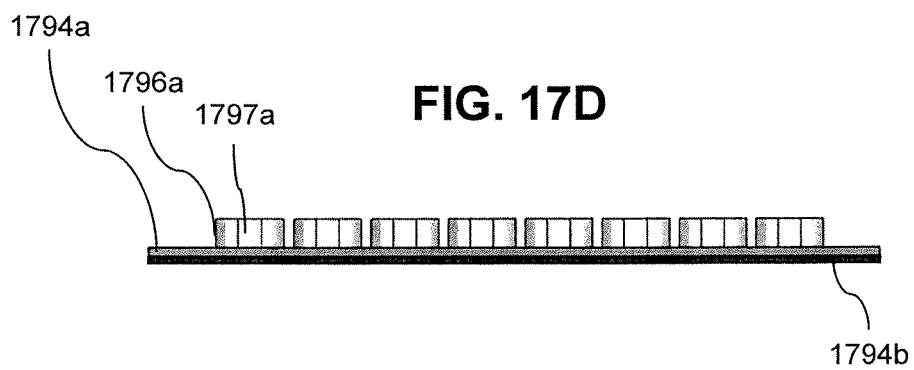

FIGS. 17A to 17D illustrate an extending cartridge syringe nest with irregular openings in accordance with an embodiment of the present invention. In some embodiments a syringe nest may have an extended configuration (for example as illustrated in FIGS. 17A and 17B) into which irregular cartridges may be inserted and/or removed from the syringe nest. The syringe nest may have a contracted configuration (for example as illustrated in FIGS. 17C and 17D) wherein the syringe nest and the cartridges fit into a standard cartridge filling machine. In some embodiments, in the extended configuration, the syringe nest may not fit into a filling machine and/or in the contracted configuration openings in the syringe nest may be partially blocked inhibiting insertion and/or removal of the cartridges. Optionally, cartridges inserted into the syringe nest are reoriented when the syringe nest moves from the extended to the contracted configuration and/or from the contracted to the extended configuration.

For example in the exemplary embodiment of FIGS. 17A-17D, two plate portions (bottom portion 1794b and a top portion 1794a) slide laterally with respect to each other. In some embodiments, in the extended configuration (as illustrated for example in FIG. 17B) bottom portion 1794b is offset to the right of top portion 1794a so that the total width of the combination is greater than the width a single syringe nest, thus the combination syringe nest in the extended configuration may not fit into a filling machine. In some embodiments, in the contracted configuration (as illustrated for example in FIG. 17D) bottom portion 1794b exactly underlies the top portion 1794a so that the total width of the combination is the width a single syringe nest, thus the combination syringe nest in the contracted configuration may fit into a filling machine.

In some embodiments, each row of orifices (for example starting with orifice 1796b) in portion 1794b are aligned with an large elongated openings 1784 in portion 1794a. Similar large elongated openings 1797a in portion 1794b are optionally aligned with the orifices 1796a of portion 1794a.

FIGS. 17A and 17B illustrate a top view and a front side view (as if looking downward from the top of the drawing along the plane of the page) respectively of an exemplary extending syringe syringe nest in an extended configuration. In some embodiments, two plate portions 1794a and 1794b may be movably joined. Optionally, in the extended configuration, orifices in portion 1794a (For example, in FIG. 17A, orifice 1796c and its associated extension) are aligned with extensions in portion 1794b (For example, in FIG. 17A, extension 1797c). Optionally, in the extended configuration, orifices in portion 1794b (For example, in FIG. 17A, orifice 1796b and its associated extension) are aligned with extensions in portion 1794b (For example, in FIG. 17A, extension 1797b). In some embodiment, the alignment of orifices with large elongated openings and/or extensions with extensions between portions 1794a and 1794b results in the openings and orifices being clear in the extended state. Optionally when the orifices and extensions are clear, an irregular cartridge can be inserted or removed through each orifice.

FIGS. 17C and 17D illustrate a top view and a front side view (as if looking downward from the top of the drawing along the plane of the page) respectively of an exemplary extending syringe syringe nest in a contracted configuration. Optionally, in the contracted configuration the extensions on portion 1794a are not aligned with the orifices on portion 1794b and/or the extensions on portion 1794b are not aligned with the orifices on portion 1794a; thus insertion or removal of a cartridge in inhibited. Optionally, in the contracted configuration orifices on portion 1794a are aligned with large elongated openings on portion 1794b and/or orifices on portion 1794b are aligned with large elongated openings 1784 on portion 1794a; thus for a cartridge inserted through the syringe nest in the extended configuration, the cartridge barrel remains inserted through the orifice in the retracted configuration with a proximal fill opening above the syringe nest and a distal end with a protrusion locked below the syringe nest. Optionally, when the syringe nest is full of cartridges (each orifice contains one cartridge) contracting the syringe nest will cause the cartridges to rotate slightly for example due to contact between the protrusion of one cartridge inserted in a orifice in one portion (for example 1794a) with a barrel of a neighboring cartridge inserted in an orifice in the other portion (for example 1794b) of the syringe nest. Optionally, when the syringe nest is returned to the extended configuration, the cartridges will be reoriented and/or can be removed.

In some embodiments, a large number of cartridges can be placed into a syringe nest in an extended configuration and then the syringe nest can be contracted facilitated tighter packing of cartridges and/or packing of more cartridges in a filling machine. Packing cartridges in an extending syringe nest optionally facilitate insertion irregular cartridges in a regular configuration that would be difficult in a static syringe nest. Some filling equipment may require cartridges in such regular configuration.

FIGS. 18A-18D illustrate an alternative cartridge mount and cartridge in accordance with an embodiment of the current invention. In some embodiments, an aperture in a syringe nest may be larger than a channel through the cartridge mount passing through the aperture. For example, the mount may include a support surface the protrudes into the profile of the aperture. Optionally the support surface may be inside the aperture, above the aperture and/or below the aperture. Optionally, a cartridge may include a fitting for hanging onto the support surface. For example, the fitting may include a protrusion and/or a groove. Optionally the fitting may be on a barrel of the cartridge and/or on a flange thereof.

Figure 18A:
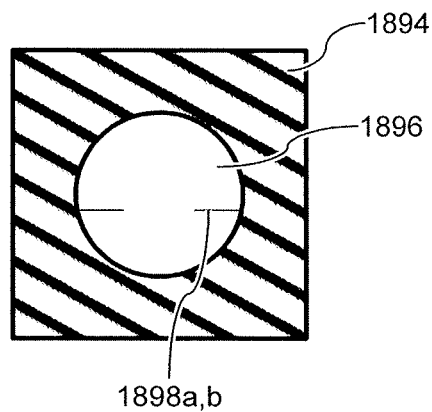
FIGS. 18A-18D illustrate an alternative cartridge mount and cartridge in accordance with an embodiment of the current invention.

In some embodiments, a syringe nest 1894 may include an aperture 1896 larger than a cartridge. A support surface 1898a optionally protrudes into a channel in the profile of aperture 1896 for example as illustrated in FIG. 18A (a plan view of a mount on syringe nest 1894). For example, support surface 1898a protrudes into aperture 1896. Alternatively or additionally, a support surface may be located above and/or below syringe nest 1894. For example, support surface 1898b protrudes into the channel below aperture 1896.

Figure 18B:
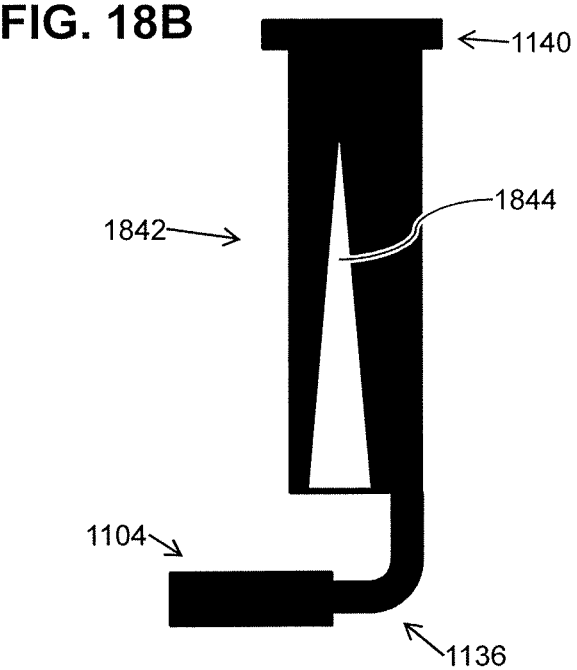
Figure 18C:
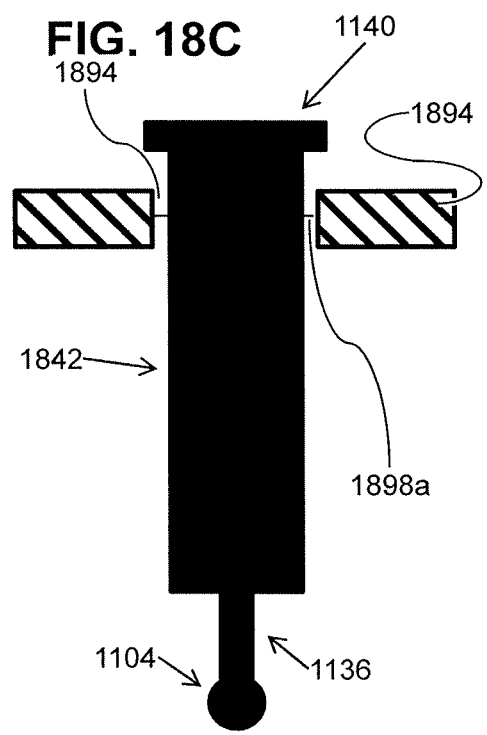
Figure 18D:
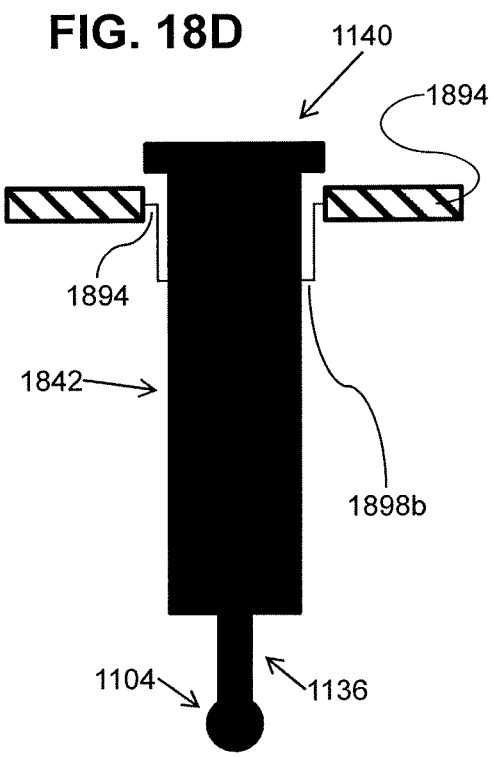

In some embodiments, a cartridge may include a groove 1844 (for example as illustrated in FIG. 18B a side view of the cartridge). For example, support surface may fit into the groove. For example, support surfaces 1898a, and 1898b include pins that protrude into dual grooves 1844 on both sides of a cartridge barrel 1842 (for example as illustrated in FIGS. 18C and 18D, side views of the cartridge in a filling syringe nest. Optionally groove 1844 is tapered such that when inserting the cartridge into the syringe nest through aperture 1896, the pin of surface 1898a, and 1898b is easily aligned with the wide bottom portion of groove 1844. As the cartridge is lowered the cartridge optionally self orients to the support syringe nest.

FIGS. 19A-19C illustrate a further alternative cartridge mount and cartridge in accordance with an embodiment of the current invention. In some embodiments, a flange 1940 on a cartridge may be supported on a syringe nest 1994 at a distance from an aperture 1996. For example, flange 1940 may include an extension 1944 that protrudes towards carrier pate 1994, at a distance from aperture 1996. For example, extensions 1944 may be oriented and/or fixed in place by an orientation feature, for example an indentation 1998 in a top surface of nest 1994. Optionally, indentation '1998 is tapered to for example with a lead in chamfer. Alternatively or additionally, extensions 1944 may be tapered.

Exemplary Dimensions of a Drug Delivery Device

In some embodiments the payload of a reservoir (for example a cartridge) may include, for example between 0.5 and 2 ml and/or between 2 and 7 ml and/or between 7 and 6 ml and/or between 7 and 10 ml of a drug and/or more. In some embodiments, the injector may discharge the entire payload as a single dose. A drug delivery device may include, for example, a patch injector, and/or an internally powered driver to drive the plunger and/or discharge the payload.

For the sake of this application, an internally powered injector driver may be defined as a drive mechanism powered by energy stored at least temporarily within the injector. Power may be stored in a power supply, for instance as chemical potential (for example a chemical that produces an expanding gas and/or a battery) and/or mechanical potential (for example stored in an elastic member and/or a spring and/or a pressurized gas). For example, the driver may be designed to discharge the payload over a time period ranging between 20 and 120 seconds and/or between 120 and 600 seconds and/or between 600 seconds and an hour and/or between an hour and a day and/or longer.

In some embodiments, the apparatus may be preprogrammed to wait a fixed time delay ranging between 2 to 20 minutes and/or 20 minutes to an hour and/or an hour to 6 hours and/or 6 hours to 2 days after activation before beginning delivery of the substance. Optionally the length of the time delay may be an estimated time for a temperature sensitive component of the apparatus to reach a preferred working temperature. For example, the temperature sensitive component may include the drug and/or a battery.

In general, discharge may be driven by a driver. An internally powered driver may be powered by various mechanisms including for example a motor as discussed, including for example a DC motor, an actuator, a brushless motor, and/or a transmission including for example a telescoping assembly and/or a threaded element and/or a gear and/or a coupling and/or an elastic mechanism (for example a spring and/or a rubber band) and/or an expanding gas and/or a hydraulic actuator).

A drug delivery device in accordance with some embodiments of the present invention may include a reservoir part as discussed. For example, a reservoir may include a medicine container and/or a cartridge. Optionally a cartridge may be preloaded with medicine using standard equipment and/or in an aseptic room. A preloaded cartridge may optionally include a proximal opening. A plunger may optionally seal the proximal opening and/or protect the sterility of the contents of the cartridge. A sterile needle, typically hollow, may optionally be connected to the cartridge barrel. For example, the hollow of the needle may be in fluid communication with the interior of the barrel.

The needle may optionally be rigidly attached to the extension at the distal end of the barrel. The sterility of all and/or part of the needle may for example be protected by a protective cap. The protective cap may remain on the needle when the cartridge is supplied and/or installed into an injector. For example, the medicine container may optionally include a cylindrical barrel rigidly attached to a needle. In some embodiments, a plunger may slide axially along the inside of the barrel to discharge a medicine payload. For example, the medicine may be discharged through the hollow needle. The protruding tip of the needle may be oriented at an angle to the axis of the barrel.

In some embodiments, the extension may include a sealing surface. For example, the surface may seal to the inner surface of a protective cap, for example a needle cover. Sealing the cap to the extension optionally protects the tip of the extension from contamination. For example, the sealing surface may have a shape that is substantially a conical section. Optionally the apex angle of the conical section may range between 0-2 degrees and/or between 2-6 degrees and/or between 6-15 degrees Optionally, the diameter of the cap mount may range between 0-3 mm and/or 3-7 mm and/or 7-10 mm and/or 10 to 20 mm. Optionally, the length of the cap mount may range between 0-5 mm and/or 5-15 mm and/or 15-20 mm. Optionally, the distance between the distal end of the cap mount and the distal tip of the extension may range between 4-20 mm as required needle insertion for a specific drug and/or injection target.

An aspect ratio of the base may be defined as the ratio of the length of the longest axis of the base to the shortest axis. Optionally the axis ratio may range between 1 to 1.5 and/or 1.5 to 2 and/or between 2 to 3 and/or greater than 3. In some embodiments, the height of the injector may range between half the length of the short axis of the base to the length of the short axis of the base and/or between the length of the short axis of the base to twice the length of the short axis of the base and/or greater than the twice length of the short axis of the base. The height of the injector may supply leverage for pivoting the adhesive off the skin of a patient after use.

In some embodiments, the force to insert the needle to the skin of a patient may range for example between 0.02 to 0.2 N and/or between 0.2 and 0.5 N and/or between 0.5 to 5 N. Optionally, the force required to inject the drug (for example the force on a cartridge plunger) may range for example between 5 to 60 N. For example the force required to inject the drug may depend on the injection rate and/or the viscosity of the drug and/or the cartridge geometry and/or the needle dimensions.

In some embodiments a needle protection mechanism may be triggered by a linear force greater than, for example, between 10 to 60 N.

For example, drug delivery device may include an auto-injector. The auto-injector may be activated by manually pushing with enough force to insert the needle. The device may then apply an injection force to inject a drug. Once the entire drug is injected and/or when there is an obstruction and/or occlusion, the injection force may rise until it passes a threshold triggering safeguarding of the needle and/or ending injection.

For example in the event of an occlusion and/or at the end of delivery, the linear force generated by the device may increase to the level of up to 60 N. A needle safeguarding mechanism (for example a needle retraction mechanism) may be sensitive to the force. For example the mechanism may include a snap that gives way at 70 N returning the needle to the retracted position.

In some embodiments, the stress to inject a medicine and/or to trigger safeguarding of a needle may include a torque. For example, injection of medicine may be driven by a plunger. The plunger may optionally be driven by a threaded assembly, for example a threaded screw and/or teeth and/or a telescoping assembly. Optionally the pitch of the teeth and/or an associated screw may range for example between 0.5 and 2 mm. The diameter of the screw may range for example between 2.5 and 15 mm. The torque to power injection may range for example between 0.2 and 1.0 N*cm. The trigger torque (the torque at which the needle safeguarding is triggered) may range for example between to 0.5 to 2 and/or from 2 to 7 and/or from 7 to 10 N*cm.

During injection, the linear movement of a plunger may range for example between 10-50 mm. The length of movement of the plunger may vary for example with the volume of medicine to be injected that may range for example between 0.5 to 3 ml.

In some embodiments, a safeguarding mechanism may be sensitive to a torque. For example, the needle may be retracted when the mechanism is exposed to a twisting moment. Optionally, discharge may be driven by a torque. For example the driver may apply torque to threaded element pushing a plunger. When the torque on the driver reaches a threshold value, the needle may be released and/or retracted and/or a needle shield may be deployed. Alternatively or additionally the trigger mechanism may require both a torque and a linear force. For example, requiring both a torque and a linear stress may prevent premature activation due to momentary friction.

In some embodiments a time of discharge may range may depend on the fill volume and/or viscosity For example the expected injection speeds may be Injection speed depend on viscosity, for example for viscosity ranging from 1 cp to 15 cp the expected injection rage may range between 30 to 70 sec/1 ml, for example for viscosity ranging from 15 cp to 60 cp the expected injection rate may range between 35 to 60 sec/ml for viscosity above 60 cp the expected injection rate may range between 53 to 67 sec/1 ml. The maximum and/or minimum expected injection time may for example be the maximum and/or minimum allowed fill volume divided by an injection rate.

For example an expected time of discharge may range for example between 24 to 78 seconds (for example for between 0.8 and 1.2 ml of fluid having a viscosity ranging between 1 to 15 cp) and/or between 36 to 68 seconds (for example for between 1.2 and 1.7 ml of fluid having a viscosity ranging between 1 to 15 cp) and/or between 51 to 92 seconds (for example for between 1.7 and 2.3 ml of fluid having a viscosity between 1 to 15 cp) and/or between 70 to 150 seconds (for example for 2.0 to 2.5 ml of fluid having a viscosity of between 15 and 70 cp) and/or between 120 seconds and 3 minutes for larger volumes and/or viscosities. In some embodiments injection times may be longer. The length of the injection time may be determined by considerations other than viscosity and/or volume.

In some embodiments the reservoir may have a length ranging for example between 20 and 72 and/or 72 and 78 mm and/or 78 and 80 mm and/or 80 and 200 mm.

In some embodiments an internal cylindrical space of a reservoir may have an average width ranging for example between 1 and 3 mm and/or 3 and 10 and/or 10 and 15 mm and/or 15 and 25 mm and/or 25 and 50 mm. Optionally a hollow space in of a reservoir may have a circular cross section such that width is the diameter of the circle. In some embodiments, a barrel section of a reservoir may have an outer width that is between 0.1 to 2 mm greater than the width of the hollow space and/or between 2 to 4 mm greater and/or between 4 to 8 mm greater. Optionally the barrel section may have a circular cross section. In some embodiments an extension may have a straight end portion with a length ranging for example between 1 and 3 mm or 3 and 7 mm or 7 and 8 or 8 and 10 mm or 10 and 15 mm or 15 and 50 mm. In some embodiments the exposed straight portion of a needle may have a length ranging for example between 1 and 5 mm or 5 and 7 mm or 7 and 10 mm or 10 and 20 mm.

In some embodiments an extension may have a sealing ring for a needle cap. The sealing ring may have a length ranging for example between 0.1 and 0.6 mm or 0.6 and 1 mm or 1 and 2.5 mm or 2.5 and 3 mm or 3 and 6 mm or 6 and 15 mm. In some embodiments a sealing ring may have an internal cavity with a length ranging for example between 0.5 and 1.5 mm/or 1.5 and 2.5 mm or 2.5 and 5 mm or 5 and 10 mm.

In some embodiments the sealing surface (for example a sealing ring for sealing to a protective cap, for example a needle cap) may have an external average width which may also be an average outer diameter ranging for example between 1 and 7 mm or 7 and 5 mm or 5 and 10 mm or 10 and 20 mm. In some embodiments the sealing ring may have an internal average width which also may be an average inner diameter ranging for example between 1 and 3 mm or 3 and 7 mm or 7 and 10 mm or 10 and 18 mm. In some embodiments, the extension may have a neck (not including the sealing ring) with an average width which may be an average diameter ranging for example between 1 and 3 mm or 3 and 7 mm or 7 and 8 mm or 8 and 16 mm. Optionally the neck may have a non-uniform cross section (for example an I beam and/or cross shaped cross section) and/or a tapered cross section.

Once the cartridge has been molded, it is optionally capped with a cap. For example, the cap may seal the distal end of the cartridge and/or preserve its sterility. In some embodiments, the extension may have a standard cap mount and/or the cap may fit over the protruding part of a needle. Optionally the cap may include a standard needle cap.

In some embodiments, a rigid cap may be rigidly mounted on the end of the protrusion. The cap optionally covers the needle and/or the end of the extension. Alternatively or additionally, the cap and/or the extension may be flexible and/or articulated. Optionally the needle cap protects the needle from contamination and/or physical damage. For example, the needle cap may seal over the end of the extension and/or the needle. The cap is optionally oriented at the same angle as the needle and/or the tip of the extension. Optionally the end of the extension is beveled and/or oriented to allow the needle cap to be pushed onto the extension and/or pulled off in the orientation direction of the extension for example between 30 and 150 degrees from the angle of the axis of the barrel of the cartridge.

Optionally, the cap will be compliant with national and/or international standards for example for protective and/or sterile needle caps for example International Standards Organization, ISO 8537:2007, ISO 594-1:1986, ISO 7864: 1993, ISO 9626, ISO 7864:1993 standards and/or other standards such as those of the US National Institutes of Health (NIH) and/or US Food and Drug Administration (FDA) and/or US National Institute of Standards and Technology (NIST). For example a needle cap may include a flexible needle shield (FNS) and/or a rigid needle shield (RNS) and/or a thermoplastic elastomer rigid needle shield (TERNS). Examples of commercial needle shields include West 7025/55 and 7025/65 and Datwyler FM 27 and Stelmi 4800 GS.

In some embodiments, a non-standard needle cap may be used. For example, the cap may be mounted at a different angle than the extension orientation and/or the needle. For example, a needle cap may fit over the distal end of the cartridge (for example the barrel of the cartridge) and/or cover the extension and/or needle. Optionally the cap may be pushed onto the cartridge and/or removed from the cartridge in a direction parallel to the axis of the syringe barrel.

In some embodiments, the cap may cover a needle and/or the extension of the cartridge, but may leave clear the proximal end of the cartridge and/or a proximal opening of the cartridge. For example, the cap may only cover a small portion of the distal side of the cartridge. For example, the cap may cover between 0.01 to 2% of the cartridge and/or between 2 to 5% and/or between 5 to 20% and/or between 20 to 50% and/or between 50 to 90% of the surface of the cartridge and/or of the length of the cartridge including the extension. Optionally, the cap covers the entire portion of the needle protruding from the cartridge.

For a non-uniform cross section an average outer width may be defined as the width of the smallest oval that can enclose the neck averaged over the length of the neck. In some embodiments a fluid path between the extension and a reservoir cavity may include a 27 gauge needle or a needle ranging between 25 and 30 gauge or a needle ranging between 20 and 25 gauge or a needle ranging between 30 and 32 gauge. In some embodiments a needle protruding from a extension may include a 27 gauge needle or a needle ranging between 25 and 30 gauge or a needle ranging between 20 and 25 gauge or a needle ranging between 30 and 32 gauge.

It is expected that during the life of a patent maturing from this application many relevant technologies and/or materials will be developed and the scope of the terms are intended to include all such new technologies and materials a priori.

As used herein the terms "about", "approximately" and "substantially" refer to ±5%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 7, from 1 to 5, from 2 to 7, from 2 to 6, from 3 to 6 etc., as well as individual numbers within that range, for example, 1, 2, 3, 7, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for filling an elongated cartridge having an opening in a proximal end thereof to an end of a cylindrical bore, the cartridge having a proximal portion, the cartridge including a lateral protrusion located distal to the proximal portion, the method comprising:
   providing a syringe nest with a plurality of apertures therethrough, wherein the plurality of apertures are arranged in a horizontal array;
   inserting said lateral protrusion and a distal portion of the cartridge through an aperture of the plurality of apertures while an axis of the cylindrical bore remains vertical, said lateral protrusion including an angled fluid path;
   hanging the cartridge from the syringe nest with said axis vertically oriented, the distal portion of the cartridge extending below said aperture, and the lateral protrusion extending laterally past an edge of said cylindrical bore;
   fixing an orientation of said lateral protrusion around said axis by interlocking the cartridge to an orientation feature on said syringe nest, wherein said orientation feature is non-symmetric with respect to 180 degree rotation around said axis of said cartridge; and
   filling the cartridge with a drug product.

2. The method of claim 1, wherein the proximal portion of the cartridge includes a flange and each of said plurality of apertures is larger than an outer dimension of the cartridge defined immediately distal to said flange.

3. The method of claim 1, wherein the proximal portion of the cartridge includes a flange and said hanging comprises hanging said cartridge by said flange.

4. The method of claim 1, wherein the proximal portion of the cartridge includes a flange and during said hanging, said lateral protrusion extends laterally beyond an outer edge of a portion of the cartridge, wherein the portion of the cartridge is immediately distal to the flange.

5. The method of claim 1, further comprising:
inserting said syringe nest into an automated filling machine.

6. The method of claim 5, wherein said aperture is larger than an outer dimension of at least one section of a barrel of said cartridge by at least 4 mm.

7. The method of claim 1, wherein a cross sectional area of each of said plurality of apertures is greater than an outer cross section of said barrel by at least 5%.

8. The method of claim 1, wherein said lateral projection includes a needle.

9. The method of claim 8, wherein an axis of a distal portion of said needle is oriented at an angle of between 15 and 150 degrees to said axis of said cylindrical bore.

10. The method of claim 8, further wherein an axis of a distal portion of said needle is oriented at an angle of between 80 and 90 degrees to said axis of said cylindrical bore.

11. The method of claim 8, where said needle is mounted to the opening on a distal face of said cylindrical bore.

12. The method of claim 1, wherein the proximal portion of the cartridge includes a flange and said lateral protrusion extends laterally beyond an edge of the flange.

13. A cartridge nest for holding a plurality of cartridges comprising:
a syringe nest defining a horizontal array of cartridge mounts, wherein each of said cartridge mounts is configured to support a cartridge, and each said mount includes:
an aperture sized and shaped to allow a distal portion of a cartridge of said plurality of cartridges to pass through said syringe nest;
a support surface shaped to prevent a proximal portion of said cartridge from passing through the aperture such that the cartridge hangs supported on said support surface and said distal portion protrudes downward through said aperture, and
an orientation feature sized and shaped to rotationally interlock with said cartridge to fix an angular orientation of said cartridge around its longitudinal axis when the cartridge is hanging from said support surface, said orientation feature making said mount not continually rotationally symmetric, wherein said orientation feature is non-symmetric with respect to 180 degree rotation around said axis of said cartridge.

14. The cartridge nest of claim 13, wherein said support surface is shaped to prevent a proximal flange of said cartridge from passing through the aperture.

15. The cartridge nest of claim 14, wherein each of said mounts is configured to support said cartridge by said proximal flange of the cartridge.

16. The cartridge nest of claim 14, wherein said orientation feature is configured to interlock with said proximal flange of the cartridge.

17. The cartridge nest of claim 13, wherein said array is symmetric to 180 degree rotation around a vertical axis.

18. A nest for an automatic cartridge filling machine comprising:
a syringe nest for defining a horizontal array of cartridge mounts, each of said cartridge mounts including:
a channel with a non-circular open cross section sized and shaped to allow a portion of a barrel of a medicine cartridge to pass through said syringe nest, said channel including a main aperture and an extension aperture, the extension aperture radiating outward from the main aperture, such that the channel has a keyhole shape, the extension aperture being asymmetric with respect to 180 degree rotation around a longitudinal axis of said cartridge; and
a support surface positioned to support said cartridge by preventing a proximal portion of said cartridge from passing through said channel such that the cartridge hangs with said proximal portion supported on said support surface and said portion protruding downward below said channel.

19. The nest of claim 18, wherein said support surface is positioned to support a proximal flange of the cartridge.

20. The nest of claim 18, further including:
a plurality of cartridges, each cartridge having a barrel including a cylindrical bore, a protrusion extending laterally beyond a side of said barrel, and a flange located proximal to the protrusion and proximal to at least a portion of said barrel; and
wherein said open cross section is sized and shaped to allow said portion of said barrel and said protrusion to pass through said syringe nest.

21. The nest of claim 18, wherein said array is symmetric to 180 degree rotation around a vertical axis.

22. A nest for supporting a plurality of cartridges in an automatic syringe filling machine, each cartridge comprising a barrel having a proximal portion, a distal portion, and a lateral protrusion extending from said distal portion, said lateral protrusion including an angled fluid path, said nest comprising:
a syringe nest for defining a horizontal array of mounts, each of said mounts including:
a channel including a main aperture having an open cross section that is larger than a cross section of said proximal portion of said barrel and sized and shaped to allow said distal portion of said barrel to pass therethrough, and an extension aperture radiating outward from the main aperture and configured to fit the lateral protrusion of the cartridge, the extension aperture being asymmetric with respect to 180 degree rotation around a longitudinal axis of said cartridge; and
a support surface positioned to support said cartridge by preventing said proximal portion of said cartridge from passing through said channel such that the cartridge hangs with said proximal portion supported on said support surface with said distal portion protruding downward below said channel.

23. A cartridge nest item of manufacture comprising:
a sterile syringe nest defining a horizontal array of cartridge mounts;
a plurality of sterile drug cartridges, each of said plurality of drug cartridges including:
a cylindrical bore having a longitudinal axis and a proximal opening;
a bent and hollow tube having a fluid path in fluid communication with and connected non-centrically to a distal portion of said cylindrical bore having a straight protruding tip portion with an axis directed at an angle of between 30 to 150 degrees to said longitudinal axis of said bore; and
a needle cap at least partially surrounding said straight tip portion, wherein each of said plurality of drug cartridges is supported from one of said cartridge mounts with said longitudinal axis directed vertically and said proximal opening facing upward.

24. The item of claim 23, further comprising:
a tub fitting around said syringe nest and protecting said sterility of said nest and said plurality of drug cartridges.

25. The nest of claim 23, wherein each said plurality of cartridge mounts includes a support surface positioned to support a proximal flange of one of said plurality of drug cartridges.

26. The nest of claim 23, further including:
a plurality of non-circular apertures in each of said plurality of cartridge mounts; said plurality of non-circular apertures sized and shaped to allow a distal portion of each of said plurality of drug cartridges and said needle cap to pass through said syringe nest.

27. The nest of claim 23, wherein said horizontal array is symmetric to 180 degree rotation around a vertical axis.

\* \* \* \* \*